(12) United States Patent
Sanders

(10) Patent No.: US 8,827,704 B2
(45) Date of Patent: Sep. 9, 2014

(54) SYSTEM, METHOD AND APPARATUS FOR IMPLEMENTING DENTAL IMPLANTS

(75) Inventor: Daniel Sanders, West Orange, NJ (US)

(73) Assignee: Mid Corp, West Orange, NJ (US)

( * ) Notice: Subject to any disclaimer, the term of this patent is extended or adjusted under 35 U.S.C. 154(b) by 19 days.

(21) Appl. No.: 13/146,038

(22) PCT Filed: Feb. 2, 2010

(86) PCT No.: PCT/IB2010/050456
§ 371 (c)(1),
(2), (4) Date: Jul. 25, 2011

(87) PCT Pub. No.: WO2010/089698
PCT Pub. Date: Aug. 12, 2010

(65) Prior Publication Data
US 2011/0287381 A1   Nov. 24, 2011

Related U.S. Application Data

(60) Provisional application No. 61/283,344, filed on Dec. 3, 2009, provisional application No. 61/270,254, filed on Jul. 7, 2009, provisional application No. 61/213,077, filed on May 5, 2009, provisional application No. 61/206,733, filed on Feb. 4, 2009.

(51) Int. Cl.
*A61C 8/00* (2006.01)
*A61C 1/08* (2006.01)

(52) U.S. Cl.
CPC ............. *A61C 8/009* (2013.01); *A61C 8/0089* (2013.01); *A61C 8/0022* (2013.01); *A61C 8/0048* (2013.01); *A61C 8/0068* (2013.01); *A61C 8/0043* (2013.01); *A61C 1/084* (2013.01); *A61C 8/0018* (2013.01)

USPC ........................................................ 433/174

(58) Field of Classification Search
USPC ............... 433/173, 174, 201.1, 172, 175, 176
See application file for complete search history.

(56) References Cited

U.S. PATENT DOCUMENTS 3,955,280 A * 5/1976 Sneer ........................... 433/169
4,713,077 A   12/1987 Small
5,116,337 A   5/1992 Johnson
5,727,942 A * 3/1998 Hartmann et al. ............ 433/173

(Continued)

FOREIGN PATENT DOCUMENTS

WO          2006/082610 A2      8/2006
WO     WO-2009002154 A1 * 12/2008   .............. A61C 8/00
WO          2010/089698 A2      8/2010

OTHER PUBLICATIONS

International Search Report dated Jul. 20, 2010 for Corresponding PCT Application No. IB2010/50456 filed Feb. 2, 2010, Published as 2010/089698 on Aug. 12, 2010.

(Continued)

*Primary Examiner* — Eric Rosen
(74) *Attorney, Agent, or Firm* — The Dobrusin Law Firm, PC

(57) ABSTRACT

A system, apparatus, device, tools and method is provided for the insertion of improved anatomically corrected modular design anterior and posterior dental implants, the apparatus including a root component and a head/abutment component, wherein the root component is inserted into the jawbone using precision surgical guide tools in combination with self-limiting surgical templates and a precision adjustable clamping device.

16 Claims, 20 Drawing Sheets

(56) References Cited

U.S. PATENT DOCUMENTS

| | | | |
|---|---|---|---|
| 5,829,977 A * | 11/1998 | Rogers et al. ................ 433/172 |
| 5,863,200 A * | 1/1999 | Hamada et al. ............... 433/173 |
| 5,871,486 A | 2/1999 | Huebner et al. |
| 5,954,769 A | 9/1999 | Rosenlicht |
| 6,017,345 A | 1/2000 | Richelsoph |
| RE36,689 E * | 5/2000 | Beaty et al. .................. 433/214 |
| 6,068,478 A * | 5/2000 | Grande et al. ................ 433/172 |
| 6,093,023 A | 7/2000 | Sala Meseguer |
| 6,250,924 B1 | 6/2001 | Luotio |
| 6,419,491 B1 | 7/2002 | Ricci et al. |
| 6,527,554 B2 | 3/2003 | Hurson et al. |
| 6,854,972 B1 | 2/2005 | Elian |
| 7,108,511 B1 | 9/2006 | Shatkin |
| 7,291,013 B2 | 11/2007 | Aravena et al. |
| 7,621,913 B2 | 11/2009 | Semet |
| 7,806,685 B1 | 10/2010 | Grant |
| 7,959,439 B2 | 6/2011 | Bulloch et al. |
| 8,231,388 B2 | 7/2012 | Grant |
| 8,287,278 B2 | 10/2012 | Grant |
| 2003/0082498 A1 * | 5/2003 | Halldin et al. ................ 433/173 |
| 2003/0180686 A1 | 9/2003 | Simmons |
| 2004/0006346 A1 | 1/2004 | Holmen et al. |
| 2004/0013999 A1 | 1/2004 | Sussman |
| 2005/0100863 A1 * | 5/2005 | Chang ........................... 433/173 |
| 2007/0059666 A1 | 3/2007 | Zickman et al. |
| 2008/0038694 A1 | 2/2008 | Tache et al. |
| 2008/0293012 A1 | 11/2008 | Chaves et al. |
| 2009/0202959 A1 | 8/2009 | Ajlouni et al. |
| 2009/0204155 A1 | 8/2009 | Aschmann |
| 2009/0286202 A1 * | 11/2009 | Ford et al. .................... 433/174 |
| 2010/0003635 A1 | 1/2010 | Feith |
| 2010/0003638 A1 | 1/2010 | Collins et al. |
| 2010/0305613 A1 | 12/2010 | Abdelgany et al. |
| 2011/0151400 A1 | 6/2011 | Boingiu et al. |
| 2011/0151408 A1 | 6/2011 | Grant |
| 2011/0159455 A1 | 6/2011 | Stumpel |

OTHER PUBLICATIONS

Written Opinion dated Jul. 20, 2010 for Corresponding PCT Application No. IB2010/50456 filed Feb. 2, 2010, Published as 2010/089698 on Aug. 12, 2010.

International Preliminary Report on Patentability dated Jul. 20, 2010 for Corresponding PCT Application No. IB2010/50456 filed Feb. 2, 2010, Published as 2010/089698 on Aug. 12, 2010.

Bergkvist et al., A Finite Element Analysis of Stress Distribution in Bone Tissue Surrounding Uncoupled or Splinted Dental Implants, Clinical Implant Dentistry and Related Research, Nov. 2008, 40-46, 10(1), Blackwell Publishing.

Lobbezzo et al., Dental implants in patients with bruxing habits, Journal of Oral Rehabilitation, 2006, 152-159, 33, Blackwell Publishing Ltd.

\* cited by examiner

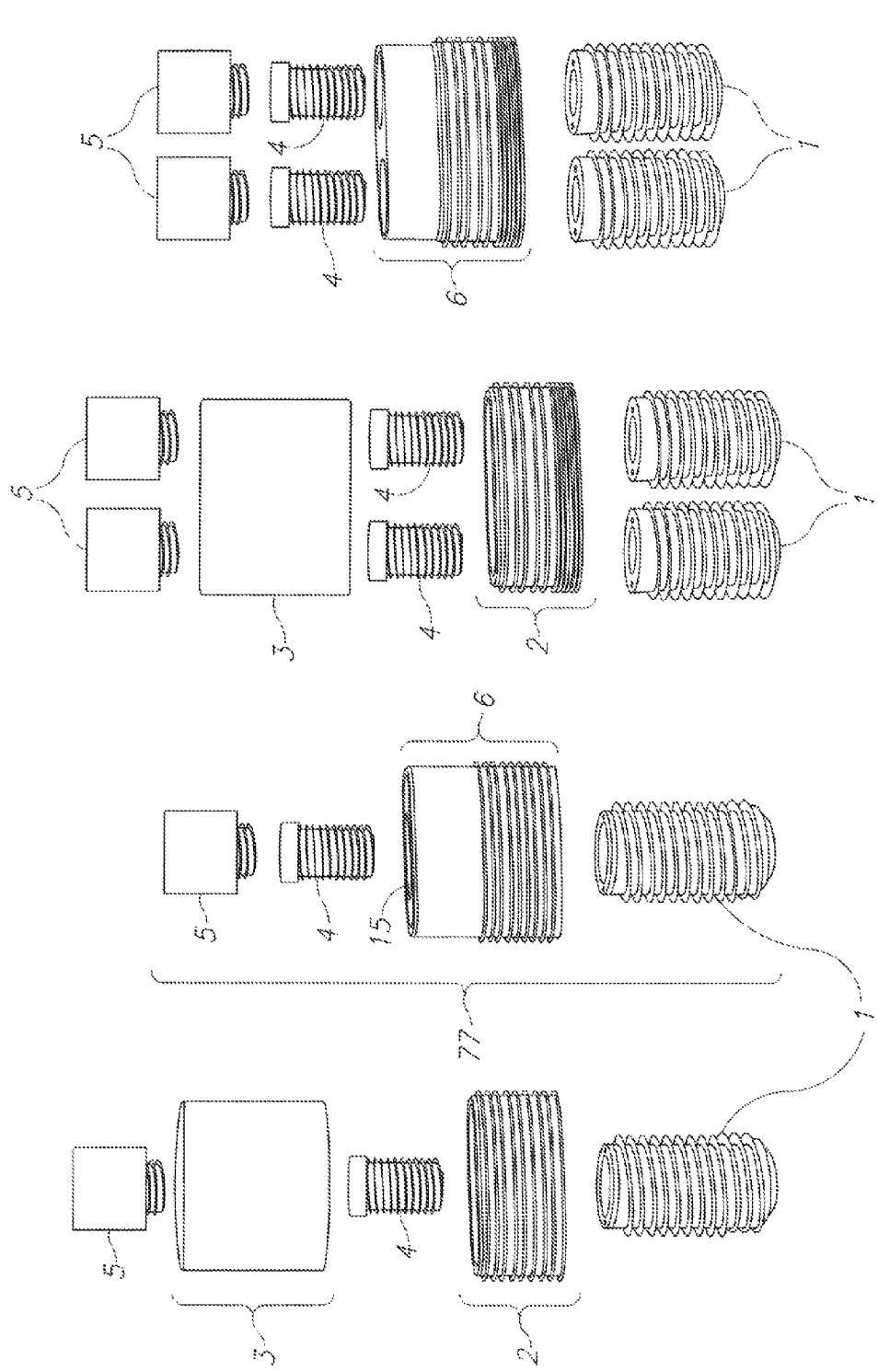

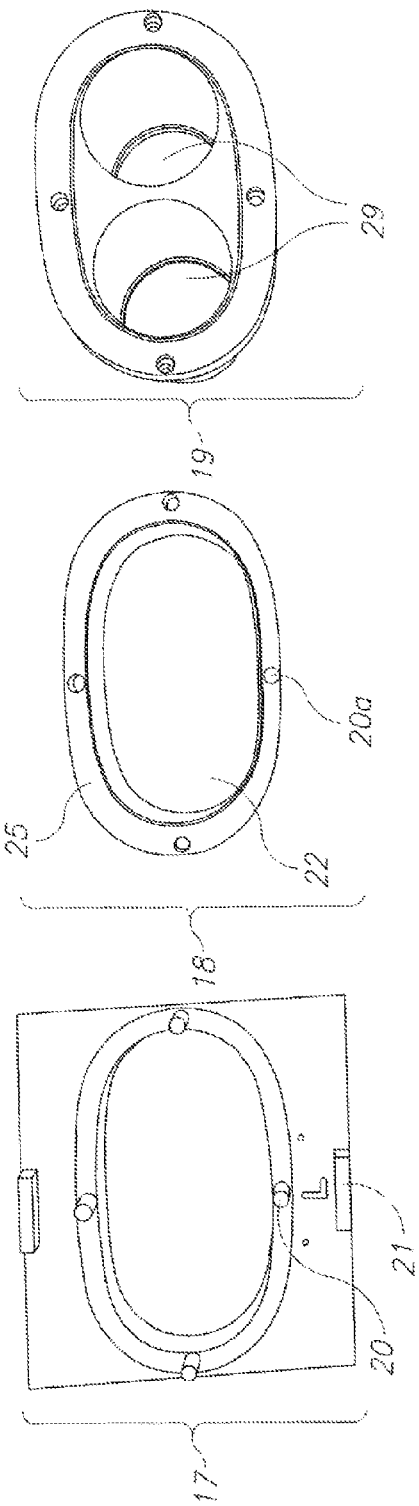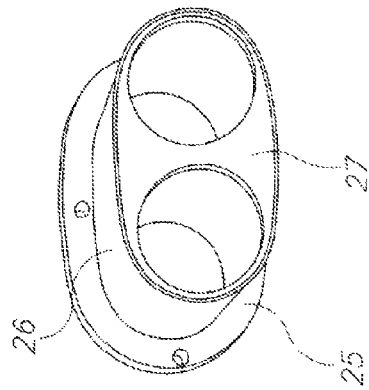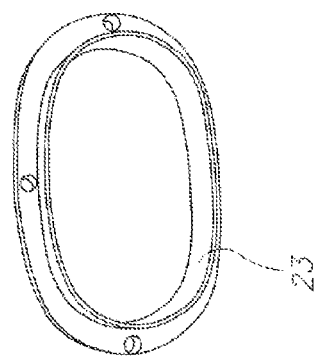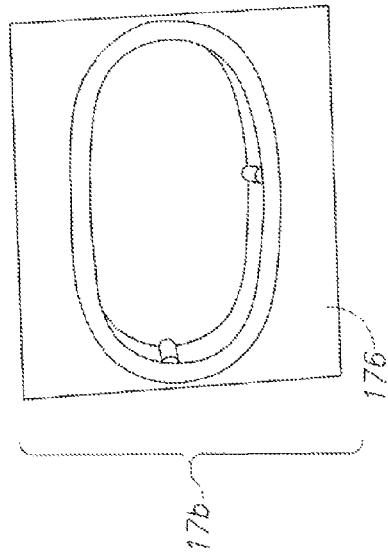
Figure 4A  Figure 4B  Figure 4C
Figure 4D  Figure 4E  Figure 4F

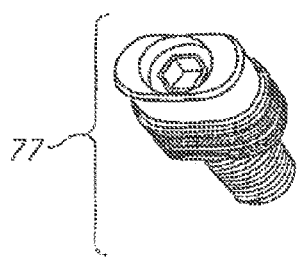 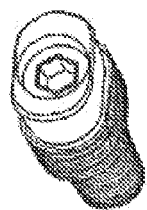 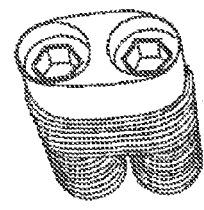
Figure 5A　　　Figure 5B　　　Figure 5C
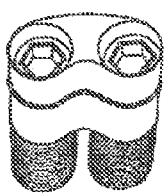 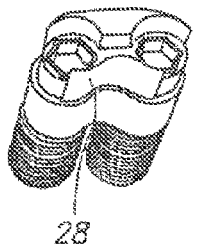 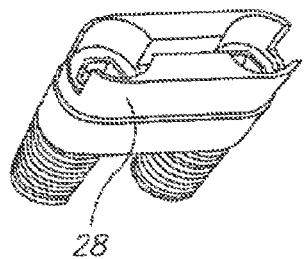
Figure 5D　　　Figure 5E　　　Figure 5F
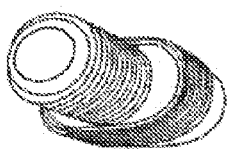 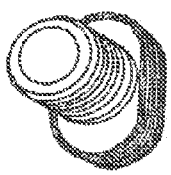 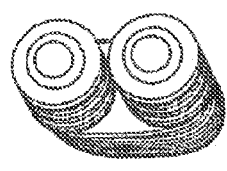
Figure 5G　　　Figure 5H　　　Figure 5I
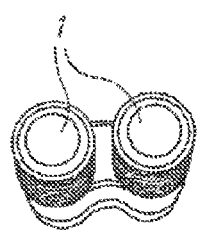 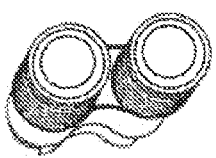 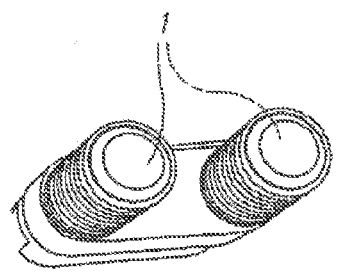
Figure 5J　　　Figure 5K　　　Figure 5L

# SYSTEM, METHOD AND APPARATUS FOR IMPLEMENTING DENTAL IMPLANTS

CLAIM OF BENEFIT OF FILING DATE

The present application claims the benefit of the filing date of PCT Patent Application Serial No. PCT/IB2010/050456 (filed Feb. 2, 2010) (Published as WO 2010/089698) and U.S. Provisional Patent Applications 61/206,733 (filed Feb. 4, 2009), 61/213,077 (filed May 5, 2009), 61/270,254 (filed Jul. 7, 2009) and 61/283,344 (filed Dec. 3, 2009), the contents of which are each incorporated herein by reference in their entirety.

CROSS REFERENCE TO RELATED APPLICATIONS

This application claims priority from U.S. Provisional Patent Application No. 61/206,733 filed Feb. 4, 2009, entitled "ANATOMICAL THREE-STAGE MODULAR DESIGN SINGLE AND MULTI-ROOTED DENTAL IMPLANT SYSTEM INCLUDING ARMAMENTARIUM", and from U.S. Provisional Patent Application No. 61/213,077 filed May 5, 2009, entitled "MODULAR DESIGN THREE-STAGE ANATOMICAL SINGLE AND MULTI-ROOTED DENTAL IMPLANT SYSTEM AND ARMAMENTARIUM" and from U.S. Provisional Patent Application No. 61/270,254, filed Jul. 7, 2009, entitled "MODULAR DESIGN THREE-STAGE DENTAL IMPLANT SYSTEM AND SURGICAL MEANS AND METHOD" and from U.S. Provisional Patent Application No. 61/283,344 filed Dec. 3, 2009, entitled "MODULAR DESIGN THREE-STAGE ANATOMICAL DENTAL IMPLANT SYSTEM, SURGICAL TOOLS AND METHOD OF IMPLANTATION" which are incorporated in their entirety herein by reference.

FIELD OF THE INVENTION

The present invention relates generally to dental implants and more particularly to an improved means and method for the preparation and insertion of an improved dental implant.

BACKGROUND OF THE INVENTION

A dental implant is an artificial prosthesis normally comprised of a single cylindrical component to replace the missing root structure of a natural tooth that has been lost. This single stage is inserted into a prepared hollowed out site (osteotomy) in the patient's jawbone (endosseous) and typically remains buried there for a period of time to allow for "osseo-integration" or the growth and adhesion of natural bone around the implant "root screw", securing it in place. This cylindrical implant typically contains down its internal center a machined threaded internal hollow sleeve that allows the dental practitioner upon later surgical exposure of the head or top section of the cylindrical implant to screw into place a machined screw-in abutment (either with an integral screw on its inferior aspect or a separate connector screw which threads through a center hollow sleeve of the abutment) or a transfer abutment screw that is modified and then sent to a dental laboratory for fabrication of the abutment. The head section of the implant is simply the top segment of the cylindrical implant form and is an integral part of it. The abutment (s), which extends into the oral cavity, is then utilized by the dentist to fabricate a single fixed prosthesis (crown), a multiple fixed prosthesis (dental bridges), or can take the form of a fixed prosthesis (over-denture bar prosthesis) to anchor a removable prosthesis such as a permanent denture, using techniques that are widely known in the dental field.

There are several major drawbacks to this standard implant design. These drawbacks are derived from the fact that the standard implant design form is actually in very significant variance to the natural root form of human teeth. There are different types of teeth in the humans, namely, the upper and lower incisors, canines (cuspids), premolars, and molars. These teeth differ to a significant degree in form from each other between the different categories, and they differ as well within each category depending on whether they are in the upper or lower jaws and which position they have in each jaw (a maxillary first molar is significantly different in form from a corresponding mandibular first molar and a maxillary second molar is different in form from a maxillary third molar). These differences in form apply not only to what is termed in dentistry as the crown portion of the teeth (the part of the tooth that is erupted into the mouth and visible to the eye) but extends as well to the forms of the root (s) portion (buried in the alveolar bone socket of the jaws) of these different categories of teeth in both the maxilla and mandible.

The distal aspects of the natural roots of teeth are basically cylindrical or somewhat oval in cross-section. When one though observes in cross-section the natural form of the roots of teeth at the level of the transition of the tooth from its root segment to its crown segment (this level is referred to in dentistry as the CEJ—cemento-enamel junction or the cervix of the tooth) one is immediately struck by the fact that in general most of the root forms in cross-section of the teeth are anything but cylindrical in shape or form (the standard dental implant form is cylindrical in cross-section along its entire length). Depending on the type of tooth in question, the natural root form of the teeth in cross-section are in fact very oval at this level (at the cervix), either in a horizontal axis in relation to the crestal bone ridge of the jaw when one is referring to incisors, or oval in a vertical axis in relation to the crestal ridge when one is referring to the premolars, and quite rhomboid, or kidney shaped when one is referring to the molars. The cross-sectional form at the level of the CEJ and particularly the dimensions of that form of each type of these natural teeth (incisors, cuspids, premolars, and molars) vary as well, depending on the jaw size and genetic variation of each individual patient. In addition, when one is referring to the molars, the natural teeth typically exhibit multiple roots (typically the molars are bi-rooted in the mandible and tri-rooted in the maxilla).

The standard dental implant design being cylindrical in form along its entire length including the head or top segment of the implant, and consisting of a very limited number of different sized single "root screw" cylinder takes none of the above-mentioned natural variation of the roots of the different types of teeth into account, both in the maxilla and the mandible.

Due to its cylindrical form along its entire length, the standard dental implant does not conform at the level of the crest of jawbone (Cervix or CEJ) to the natural oval, rhomboid or kidney-shape form of the roots of the natural teeth (the head of the implant is cylindrical in cross-section). This major discrepancy in the contour or emergence profile, as it is termed in dentistry, of the crown that is fixed upon the implant abutment (which fits into the head of the implant) in relation to the gums results in large gaps or spaces between the implant crown and the teeth on either side of it and prevents the optimal formation of the interdental papilla (gum tissue between the teeth). With the posterior implant, the situation is very much analogous to a large ball sitting on top of a thin stick. These large open areas or gaps allow for food debris, plaque, and pathogenic bacteria to accumulate between the implant crown and the natural teeth adjacent to it, making these areas very difficult for the patient to keep clean and requiring the patient to use special cleaning implements to try and maintain them free of food debris and plaque. In many cases this situation over the long-term results in poor health of the gums, causing periodontal (gum) disease of the adjacent teeth as well as documented cases of implant failure due to crestal bone resorbtion.

Additionally, as was previously mentioned, all standard implants on the market consist of a single cylindrical "root screw" form or stage that is buried into the alveolus (jawbone) to replace the natural root of the missing teeth. A second stage abutment is later screwed into the "root screw" (the abutment sits above the bone in the mouth) and a crown is made to sit on top of the abutment. This represents your typical standard two stage implant (the crown is never considered as a stage of the implant). Recently, one stage implants have been designed where the root screw stage and the abutment stage are all one integral piece. These are almost exclusively being used at present for the replacement of missing anterior teeth only.

This accords to a relatively good degree for the replacement of all the anterior teeth in the mouth but is not at all in accord with the natural state for replacing the posterior teeth, where as was previously mentioned, the upper molars are typically tri-rooted and the lower molars are typically bi-rooted.

The reason why providence formed these molar (posterior) teeth with multiple roots is that these teeth are designed to take on the entire burden of grinding and chewing most of the food we eat and they also are designed to maintain the proper vertical jaw relation between the upper and lower jaws, referred to in the dental field as the Vertical Dimension of Occlusion (V.D.O.C.), or maintaining the proper "bite". Multiple rooted teeth versus single rooted teeth offer the advantages of spreading this intense load more efficiently as well as providing far greater stability from tipping or shifting the position of the teeth under load. They also provide vastly greater anchorage of these posterior teeth in their jawbone sockets as they engage a far greater surface area of bone buried in their multiple bone sockets. Because the load is distributed more efficiently, each singular root of these multi-rooted molars is individually thinner, shorter, and therefore smaller than would be the case if these teeth had instead been formed in the natural state with a longer, thicker and therefore larger single root buried in a single larger bone socket.

Standard implants with their single "root screw" design best tolerate compressive loading forces. Compressive forces are forces that are apically directed along the long axis of the implant. Tensile forces are forces that are coronally directed along the long axis of the implant and are not tolerated well by the implant. Shear forces are off-axis forces or loads on the implant that have the potential to be most destructive to the integrity of the implant-bone complex. Due to their single "root" design, standard implants placed in the molar (posterior) areas of the mouth are most susceptible to the negative effects of shear off-axis forces. Crater-shaped bone defects which are typically found clinically to form around the "heads" (top portion of the implant embedded in the bone) of these implants over time are suspected to be a result of such adverse loading. (G. Bergkvist, DDS. Dept. of Dental Materials Science, Malmo University, Sweden 2007).

Stress forces when an implant is "loaded" are known to be concentrated at the "head" or top part of the implant that is buried in the bone. The relatively narrow cross-sectional diameter of the single "head" of most dental implants does not allow for the proper distribution of this load for molar implants. Between 10-20% of the adult population are bruxers, people who habitually grind or clench their teeth to reduce stress (J. Oral Rehabilitation, 2008).

The average standard implant (two-stage) can take a vertical (compressive) loading force of 450 pounds per square inch or 32 kilos per square centimeter. The average bruxer generates a vertical (compressive) loading force of up to 600 pounds per square inch or 42 kilos per square centimeter, a figure well in excess of what the standard dental implant can comfortably handle over time. As noted above, vertical (compressive) loading forces are the forces best handled by standard dental implants, as opposed to shear (off-axis) loading forces which are much more damaging over the long term to the integrity and viability of the standard dental implants (and particularly standard posterior molar implants) in the mouth.

Splinting (connecting together) implants has been proven to reduce stress over unsplinted implants by a very large factor (Univ. of Malmo, Sweden 2007).

On an evolutionary level, the upper and lower jaws have adapted anatomically over a vast time period to the thinner, shorter and therefore smaller natural root form of the multi-rooted posterior molars by lightening the weight of the human skull and its considerable load on the spinal column in the following manner:

The upper jaw (maxilla) in the molar(s) region contain empty spaces called sinuses immediately above and in many cases actually wrapping around the tips of these multi-rooted teeth. In the lower jaw there is a marked sloping in or reduction in the width of the mandible on both the buccal (cheek-side) and lingual (tongue-side) of the bony plates from the crest of the jawbone to the inferior line of the mandible. Additionally, the inferior alveolar nerve runs in a canal in the mandible in an inferior position to the lower teeth.

All of the above presents significant challenges to the dental practitioner when attempting to replace these missing posterior teeth with the standard dental implant design. Due to their single large cylindrical "root" form, the anatomy of the upper and lower jaws can be particularly unsuitable to accommodate the standard dental implant design in these molar regions. This is because typically the standard posterior implant dimensions are 4.7 millimeters in cross-sectional diameter and 13 millimeters in overall length. These dimensions are necessary in order to place an implant of sufficient size that can reasonably handle some of the forces of the load placed upon it in the posterior upper and lower jaws.

This unsuitability of design is the case even more so in patients who have large maxillary sinuses in the upper jaw or crestal height resorbtion of the maxilla or mandible (a very common finding in patients who have previously lost their molars). These particular cases typically require additional surgical procedures such as maxillary sinus lifts (42% of maxillary posterior implants required sinus lifts in a retrospective seven year study published in the Journal of Periodontology, 2008) or maxillary and mandibular crestal ridge augmentation in order to make these sites better suited to accommodate the physical dimensions of the standard dental implant (provide sufficient depth of bone at the implant site so as not to puncture the sinus). These procedures are costly and are associated with concomitant health risks to the patient. Often these anatomical limitations may force the dentist to place the implants in a non-optimal location or if the limitations are severe, they may totally preclude the patient from receiving this restorative treatment option altogether.

The dentist also runs the general risk in many cases of perforating the maxillary sinus (compromising its health), perforating the lingual or buccal plates of the mandible (causing infection and implant failure), or disturbing or partially severing the inferior alveolar nerve in its canal in the mandible (causing a temporary or permanent parasthesia) when attempting to place a standard posterior dental implant.

Bone quality and volume are of paramount importance to the dental surgeon placing implants. It is important for the dentist to consider bone quality from a biomechanical standpoint. Generally, the anterior mandible has the densest bone followed by the posterior mandible and then the anterior maxilla, with the posterior maxilla being the least dense. Low density bone requires a longer healing period to maximize bony adaptation to the implant surfaces.

The upper and lower jaws are made up of a narrow strip of softer, spongy, alveolar bone sandwiched between two outer thin hard cortical plates of bone. In the posterior regions the entire width of the jawbones is typically 5 to 7 millimeters thick. The average interdental (between the teeth) space remaining when a molar tooth is lost is 10 to 12 millimeters long. The vertical depth of alveolar bone present where the tooth was lost can be as little as 5 to 10 millimeters before one encounters either the maxillary sinus space (in the upper jaw) and the inferior alveolar nerve (in the lower jaw).

Additionally, as was noted above, the loading force on these posterior teeth (molars) is much greater than the loading force placed on the anterior teeth. For this reason the diameter of the standard implant used to replace these missing teeth is significantly larger than the diameter of the implants used to replace missing anterior teeth.

To allow for a proper volume or thickness of jaw bone between the implant and the adjacent teeth so as to allow for a proper blood supply and health of the bone between the implant and the adjacent teeth, it has been accepted in the dental field to maintain a minimum distance of 2 millimeters between the implant and the adjacent teeth on either side of the implant. As noted above, this means that the head of the implant at the height of the crestal bone should not exceed a diameter of 6 to 8 millimeters in a mesio-distal dimension (the distance between the adjacent teeth where the missing tooth used to be), based on the formula: interdental space (space left by the missing tooth) minus 4 millimeters (2 millimeters on each side of the implant)=maximum diameter of implant head. In the particular case of the posterior teeth (molars) it is typically either 10−4=6, or 12−4=8. As mentioned above, the entire width of the jawbones is typically between 5 to 7 millimeters thick (referred to in the dental field as its Bucco-Lingual dimension) in the posterior area. This means that in order to stay within the confines of the jawbone and not puncture the outer cortical plates of the jawbone, the maximum dimension of the head of a standard implant which is round in cross-section should typically not exceed 6 millimeters in diameter.

In addition to the above space requirements and limitations, it is well known in the dental field that a minimum distance must be maintained between multiple implants as well (distance between one implant and the next when placing two implant next to each other) in order to maintain the proper bold supply to the bony tissue between the implants and prevent resorbtion or "die-back" of said bone.

Several systems have been developed to try and mitigate some of the significant drawbacks of the standard "single root" dental implant design described above. To better approximate the natural form of the root of the tooth at the cervical junction, an example of this is a one-piece dental implant as described in U.S. Pat. No. 6,854,972, February 2005, Elian, wherein a flaring cervical portion is incorporated in the proximal (coronal) end of the implant.

U.S. Pat. No. 6,093,023, July 2000, Meseguer, describes an implant with an "external" polygonal "head". This is a confusion of terminology as what is being described is a polygonal abutment which is external (above the crestal height of the jawbones) to the endosseous implant. The actual "head" of the implant embedded in bone is round in cross-section (not polygonal), and an integral part of the "body" of the "root screw" component. This implant aims to provide a more anatomical shape for the abutment and a better esthetic result for the "peri-implant" (gums) soft tissue.

U.S. Pat. No. 7,291,013 November 2007, Aravena and Kumar, describes a standard single root form implant similar to U.S. Pat. No. 6,854,972, yet with a more pronounced anatomical flaring of its coronal segment or "head" as well as a more flared "abutment" component that closely matches the contour of the "head". It still maintains a round cross-sectional form of the integral head of the "single-root" implant.

In an attempt to improve soft tissue attachment, U.S. Pat. No. 6,527,554 March 2003, Hurson and Dragoo, describes a roughened zone on the coronal head of a standard single-root form implant to better preserve the "biological width" or "attachment zone" between the implant-abutment interfaces.

U.S. Pat. No. US 2010/0003638, January 2010, Collins, Flynn, and Murray, describes a modular "single-root" implant design which includes a "head" an intermediate part which is porous in an attempt to better engage bone, and on its inferior aspect a short length threaded "screw" segment. While the intermediate (middle) section may possibly enhance bone adhesion over the long term, it does so at the expense of allowing for the initial "bite" into the osteotomy bore shaft and initial fixation of a standard "root screw" which features a threaded screw form down most if not all of its length.

In an attempt to provide for a multi-rooted tooth form implant, WO Pat. App. No. 2006/082610 August 2006, Cito, D'Ambrosio and Vinci, describes a "multiple-root" form dental implant design with a "head" component which it calls a "collar" and a "root screw" component which it calls a "fixture". For the sake of clarity the terms "head" and "root screw" used by the present invention for these components will be used to describe these components in regards to this prior art.

This prior art is very limited in its design and incorporates as well significant structural defects that could compromise its short and long term viability in the mouth and could actually cause over time a catastrophic failure of the components of its separate stages as will be explained below. Additionally, the tools described in this prior art do not allow for the accurate, precise, and reproducible preparation of the implant site as well as the accurate, precise, and reproducible assembly of the components of the implant within that site in a three-dimensional manner.

This prior art describes a design wherein the "root screw" components are by necessity of smaller diameter or girth than the attachment (connector) holes of the "head" component as they need to be inserted through these holes and then via an extending circumferential lip on its superior aspect of greater circumference (which acts as a limiting stop) engages the smaller circumference of the insertion hole of the "head" component in order to relate these two components to each other.

This is a significant drawback in the structural design of the prior art for the following reasons: As noted above, there are significant limitations on the maximum interdental (mesio-distal distance between the teeth) and bucco-lingual (width of the jawbone) dimensions of the implant site. The diameter of the "head" component that can typically be accommodated in this limited implant site for missing molar teeth without puncturing this three-dimensional volume of the bone in both of the above two dimensions is itself quite limited. Therefore, the attachment (connector) holes contained within it must of necessity be of smaller diameter than the "head" which contains them.

By incorporating in its basic design a "root screw" that must of necessity be of smaller diameter than the retention hole of the "head" component into which it slides through requires the "root screw" component of this prior art to be extremely "thin", resulting in a critically insufficient diameter or girth for these "root screw" components. As these "root screw" components are the primary structures of the implant that provide the retention, stability and load support for the entire implant, this design flaw is of critical importance and would jeopardize the long term and even short term viability of this implant design in the mouth (as noted above, it is accepted in the dental field to always use larger diameter single "root screws" for posterior implants compared to anterior implants due to the greater forces normally placed on the posterior implants). The inadequate diameter of these "root screws" is even more problematic when one considers the fact that all "root screw (s)" do not have a solid core and in fact must contain an internal hollow shaft to accommodate the connector screw which threads into it. This means that the thickness of the outer walls of the "root screw" design of this prior art must be extremely thin and would be very prone to fracture (resulting in complete failure of the implant) under even a minimal load.

Additionally, the very small diameter of the "root screw" components necessitated by the design of the prior art also necessitates that the single set of "connector screws" provided by the prior art to secure all three components (the "head", "root screw" and abutment components) to each other to be even thinner than the "root screws" (as they must thread inside them), which, over time, (or even on initial load) could easily lead to their fracture under load. This would cause a separation of these two components within the jawbone, resulting in the complete failure of this implant design and a nightmare scenario for the dental practitioner to have to deal with.

Additionally, the abutment stage design of this prior art describes projecting tubes on the bottom surface of the abutment which extend through the retention holes in the head stage and the center shafts of the "root screw" stages in order to relate these components to each other. This design feature further limits the maximum possible diameter of the connector screws and also necessitates the further thinning of the outer walls (which contain the connector screw) of the "root screw" components. These design features even further increase the likelihood of the fracture and failure of these components, above and beyond what has already been noted, when these components would be placed under load in the posterior sections of the upper and lower jaws.

As mentioned above, the accepted protocol in the dental field is to allow for the endosseous (embedded in bone) elements of the implant to osseointergrate (solidify by allowing for the intimate bone adhesion to their surfaces during the healing process). This protocol of waiting for healing for several months duration is especially applicable to posterior (molar) implants due to the poor bone quality in these posterior regions of the jaws and the greater load these implants must support once they are placed under loading function (chewing on the crown atop their abutments).

In the prior art the "head" and two "root screw" components only passively connect to each other via a small self limiting flange or lip on the superior end of the "root screw" embodiment of the prior art at the time of the initial primary implant surgery procedure and are only secured to each other actively (with the single set of connector screws provided) after the entire healing period has elapsed and the dentist performs a small secondary surgery in order to gain access to the superior aspect of the "head" component so that he can secure the third abutment stage to the implant components that have already been embedded in the jawbone.

This means that during the extensive healing period, shifting is likely to occur between the "head" and two "root screw" components of the prior art (which are only passively connected to each other during this entire healing period) as the bone actively remodels around them and fixes these two components rigidly in their final position in the bone. This shifting and fixing in place of the shifted position of these components within the bone during healing may result, in the prior art, in a loss of parallelism of the "head" and "root screw" components of the prior art and therefore may not allow for the insertion of the two internal sleeves or tube features described on the inferior aspect of the abutment stage of the prior art into the corresponding two retention shafts of the "head" and "root screw" components. This would present an extreme problem for the dental practitioner to properly assemble the components of the prior art's implant and which might even necessitate the surgical removal of the implant, a highly undesirable result. If the shifting is minimal it still may require the dentist to use excessive force in order to screw down one or both of the connector screws through the now non-parallel shafts between these components. The forceful screwing of these two connector screws into the non-parallel shafts may compromise the integrity of the implant of this prior art, as it will place undue stress on the components and surrounding bone, and may result in bone resorbtion (die-back) and long term failure of the prior art's implant.

Drawbacks of the Surgical Tools: While WO Pat. App. No. 2006/082610 does describe a basic template guide for drilling the bore shafts to allow for the placement of the "root screw" components, its surgical template does not allow for preparing an accurate and precise depth and position of the bone preparation of the "head" component, and so does not allow for the accurate and precise insertion of these components in a reproducible fashion by the dental practitioner in the implant site.

This is due to the lack in this prior art of any form of clamping device to accurately and precisely fix the template over the implant site to allow for just such an accurate preparation of the bone at the implant site to receive both the "head" component and "root screw" components of the implant. As noted above, this is an absolutely critical requirement for any implant system to be successfully placed in an accurate and repeatable fashion in relation to the adjacent teeth or specific location in the jawbone deemed most advantageous by the dental practitioner for the insertion of the dental implant based on various diagnostic criteria known in the field. This prior art fails to achieve this basic requirement and so is impractical for the use of the dental practitioner who wishes to place implants with a high success rate.

It is important to note as well the method for preparing the osteotomy and inserting the components of the multi-root three-stage implant described in WO Pat. App. No. 2006/082610 into the osteotomy at the implant site, as there are further significant drawbacks in this method of preparation for receiving in the implant site the design of the multi-root components of this prior art, as well as the actual design form of the multi-root implant components described in this prior art.

WO Pat. No. 2006/082610 allows for the preparation and insertion of one and only one "head" stage form (component) in the implant site, and only for "multiple" rooted implants, a distinct disadvantage. This is due to the fact that this prior art describes only one template form that allows for the creation of bone preparation holes to accommodate this one particular "head" stage form (component).

A further major drawback of the entire prior art (including this particular prior art) is that they do not allow for surgical templates that allow for the placement of different mesiodistal length "heads". The prior art does describe one other alternate shape (elliptical) for the "head" stage form (component) but provides no means for preparing the implant site to accommodate this other shape, a serious drawback of the prior art. Additionally, the cross-sectional shape of the particular "head" component described in this prior art for which it does provide a basic means for preparing the bone site to accommodate its form, does not conform to the natural cross-sectional form of any of the natural molars at the crestal height of the bone (the level of the implant-abutment interface, known in the dental field as the crucial "biological width" or attachment zone) and is therefore a poor choice of "head" form (component) from a biological perspective to implant into the posterior jawbones.

The above elements described may be critical requirements, as noted above, for the successful implantation of any dental implant and are actually more critical requirements for the successful placement by the dental practitioner and long term viability of a "multi-rooted" posterior (molar) implant due to the larger number of components (compared to a "single-rooted" anterior implant) which must accurately be related to each other and related to the bone preparation fashioned to receive them. Additionally, a posterior molar implant should be able to handle the significantly greater amount of load (stress forces) it must withstand due to its position and normal function requirements (holding up the bite and chewing forces).

U.S. Pat. App. No. US 2010/003635, January 2010, Feith, describes a "multi-root" implant based on a physical composition of zirconium oxide as opposed to the standard titanium or titanium alloy. This is based on a "one-piece" design of the entire implant (roots, and abutment). The multiple "roots" described are not threaded (screws), their "heads" are integral part of their "roots" and their center axes are parallel to each other to allow for a straight path of insertion.

In an attempt to provide for a more anatomically correct abutment form for posterior teeth (molars), U.S. Pat. App. No 2008/0293012, November 2008, de Resende Chaves and Martinez describe a splint abutment component for a single stage "root screw" form of a two stage dental implant. This design in fact results in a biomechanical disadvantage over the previous art as it embodies a wider platform (known in the dental implant field as platform switching) for occlussal loading (chewing) which then narrows to the standard round cross-sectional diameter of a standard "head" of a standard dental implant. This exaggerated platform switching design (compared to the other prior art) may actually lead to increased bone loss, known in the dental filed as "craterization" or "saucerization", a well known deleterious consequence commonly found in the bone surrounding the "heads" of all the current prior art once the molar implants are placed under occlussal load for a sufficient period of time in the oral cavity. This "craterization" is due to the "overloading" of the "head" of the implant which caused the bone to die back or resorb.

Surgical Guide Clamps: U.S. Pat. App. No. US 2004/0013999, January 2004, Sussman, and U.S. Pat. App. No. US2009/0202959, August 2009, Ajlouni and Adjlouni, both describe a surgical guide clamp to be utilized to guide the bone drills in the preparation of the osteotomy at the implant site. U.S. Pat. App. No. US2004/0013999 describes a basic cylindrical ring form from which projects a horizontal cross-member. From this horizontal cross-member project, at right angles to it, two short bars with "teeth" on their inferior aspect to engage the vestibular regions of the jaw bone. This prior art offers no features to adjust the location of the guide ring in any of the three axes, nor does it take into account the adjacent teeth, which, based on its design dimensions, would interfere with its placement between the adjacent teeth in close proximity to the surface of the intended implant site. The guide ring of this prior art also only allows for the preparation of the standard round cross-sectional form for the entire length of the implant body (standard implant form).

U.S. Patent App. No. US 2009/0202959 is an advancement on the basic design of U.S. Pat. App. No. 2004/0013999, as it does allow for the accurate adjustment of its ring shaped guide form in three axes, and attaches with clamping members to the adjacent teeth on either side of the implant site. This design though, does not allow for the clamping of the device in the very common situation requiring dental implant restorations, of what is termed in the dental field as a "free-end saddle" case. This is a situation where there is a missing tooth or teeth space(s) behind (distal) to whatever is the terminal tooth in that arch or quadrant of teeth of the jawbones (upper and lower). Additionally, the design of this prior art does not contain a swiveling feature as does the present invention in order to rotate its ring guide in an off-axis manner relative to the width and length (bucco-lingual and mesio-distal) dimensions of the alveolar ridge at the proposed implant site. The guide ring of this prior art also only allows for the preparation of the standard round cross-sectional form for the entire length of the implant body (standard implant form).

SUMMARY OF THE INVENTION

Systems, means and methods for the preparation and insertion of improved anatomically corrected implants that more closely imitate the overall natural form of the root system of human teeth. In some embodiments this system includes two detachable modular stages with customizable features to which a third abutment stage is attached or alternatively, is an integral part of one of the two stages.

Moreover, in accordance with an embodiment of the present invention, a modular design two stage multi-root dental implant system is provided, comprising multiple detachable and modular stages which are placed endosseously, including a first stage including multiple root screw components, and a second stage including a head/abutment stage, where the head and the abutment components are integrated.

According to some embodiments the head component and the abutment component are configured as separate stages. In some embodiments a unified overdenture multi-attachment element is secured to the multi-stage multi-root implant. In further embodiments the modular design dental implant system includes multiple cylindrical root screws that are placed endosseously, where these screws provide a splinting effect when coupled with a second stage. In yet other embodiments the head/abutment stage includes side walls that conform at the level of the cervix to the natural root form of a selected tooth type, and conform to the natural differences in root form of these different types of teeth at the level of the cervix of the upper and/or lower jaws.

In further embodiments the head/abutment stage includes multiple connecting holes for the secure attachment of the first and second stages. In other embodiments the modular multi-stage dental implants are adapted so that a separate abutment stage "sinks" into the separate "head" stage, thereby allowing the abutment to sit below the crestal height of the upper and lower jawbones. In additional embodiments the dimensions and/or placement directions of each of the multiple root screws is parallel or offset from each other, and/or may be attached in parallel and/or otherwise angled to the "head/abutment" stage. In further embodiments the head-abutment stage is split into two stages, and the head component is adapted to allow the intimate fit of the abutment component within the second stage. In other embodiments the head and/or abutment components include micro-grooves and ridges on the external surfaces to enable enhanced retention and/or bone adhesion.

In further embodiments the head stage includes hollowed out internal anti-rotational rings and internal projecting rings, thereby enabling the abutment stage to be coupled to the head stage with anti-rotational features. In yet other embodiments the first stage and second stage can be intimately fitted and attached into each other via fitted sleeves and collars to minimize micro-gapping between the stages. In some embodiments the intimate fitting mechanism includes internal threaded screw retaining components to provide tight sealing. In yet additional embodiments an adjustable over-denture bar assembly is provided with adjustable locking features, adapted to fit into multiple abutment components that have cut out proximal areas for the insertion of multiple rotatable and adjustable length over-denture bar components. In some embodiments multiple separate over-denture attachment elements are secured to the multi-stage stage multi-root implant.

Furthermore, in accordance with an embodiment of the present invention, a modular design two stage single root dental implant system is provided, comprising two detachable and modular stages which are placed endosseously, wherein the first stage includes a single root screw component, and the second stage includes a head/abutment stage, wherein the head/abutment stage integrates a head component and an abutment component. In some embodiments the head/abutment stage includes a single connecting hole for the secure attachment of the first and second stages. In further embodiments the head component and the abutment component are configured as separate stages. In additional embodiments the single root screw stage attaches to an anatomically more correct anterior head stage for anterior dental implants. In other embodiments the single root screw stage attaches to an anatomically more correct head stage for posterior molar implants where the mesio-distal bone volume width of the edentulous implant site does not allow for the placement of multiple root screw components.

According to some embodiments, an implanting apparatus is provided for implementing the preparation of the osteotomy and placement within the osteotomy of modular design multi-stage dental implants, the apparatus including surgical templates and surgical clamps. In some embodiments the surgical templates include self-limiting dental implant drills, implant guide pins, and implant component drivers, where the drills, pins and drivers are designed to be used in conjunction with the surgical templates and the surgical clamps. In still further embodiments the surgical clamps include a precision adjustable clamping device adapted to clamp directly into the concave undercuts of the gingival vestibules of the oral cavity, thereby enabling a temporary rigid fixation of the clamp in the vestibules. In further embodiments the surgical clamps include a precision adjustable clamping device adapted to clamp directly to at least one tooth adjacent to the implant site.

According to some embodiments, a system is provided for implementing over-dentures, comprising an adjustable over-denture bar assembly with adjustable locking features, the bar assembly including multiple adjustable over-denture bar components that can be fitted into multiple stage implants so that the assembly can secure a full denture in an edentulous patient. In further embodiments the multiple stages include a head stage and an abutment stage being separated into two stages.

According to some embodiments, an apparatus for the insertion of improved anatomically corrected dental implants is provided, comprising a root component and a head/abutment component, wherein the root component is inserted into the jawbone using precision surgical guide tools in combination with self-limiting surgical templates and a precision adjustable clamping device.

In some embodiments the head/abutment component includes a separate head component of various geometrical cross-sectional profiles and a separate corresponding abutment component of various cross-sectional profiles. In further embodiments the root component is adapted to be inserted into the bone to an exact proper vertical depth within a bore shaft(s) when utilized in conjunction with a self-limiting "root screw" driver, so that the root component can be accurately and intimately coupled to the head/abutment component. In other embodiments the root component includes multiple root screws, wherein the root screws are splinted together with said head/abutment component, so that said splinting together provides expanded implant to bone interface so that the root component strength is compounded and the entire fully assembled implant strength and durability is compounded. In further embodiments the root component is modified to provide a selected form which is optimized for the target bone area, such that the root component(s) is/are of an optimal size and strength in relation to the available treatment area. In additional embodiments the head component is adapted to be placed in the bone, and has an internal extensive hollowed out area encompassing a large percentage of the inner surface area of the head component, thereby providing for far greater frictional fit, enhanced anti-rotational function, and a wider and more uniform distribution of the forces of mastication over the entire structure of the implant. In still other embodiments the abutment component is adapted to be coupled by its insertion within a "basket" form within the hollowed out area of the head component, so that the frictional surface area of the coupling is maximized, thereby minimizing the micro-spaces and rotational space between the components. This relation of the abutment and head components allows for the transfer of the functional and parafunctional loading forces into the surrounding bone in a more biologically healthy manner.

In further embodiments the head/abutment component incorporates on its outer surfaces micro-threads to enhance primary fixation of the implant, thereby allowing for immediate loading of the implant substantially at the time of the primary implant procedure. In other embodiments the head/abutment component includes an underside collar/rings which is/are related in an intimate manner, from below, to the root component(s), thereby preventing the need for the root component to be threaded through the retention holes of the head component, such that the root component(s) is of a significantly greater diameter than the retention hole of the head component. In other embodiments the surgical guide tool is adapted to enable precise depth drilling according to a three dimensional space plan, so that the root bore hole drilled is optimized within the target bone area. In further embodiments the surgical guide tool is adapted to enable precise drilling according to a three dimensional plan, so that the upper portion of the osteotomy can be precisely prepared for the insertion of the variously shaped head/abutment components within the target bone area.

In other embodiments a precision adjustable clamping device is adapted to enable adjustable yet precise drilling into a target bone area, so that the root bore hole drilled is optimized within the target bone area, the clamping device being usable whether the patient has adjacent support teeth or has no adjacent support teeth. In other embodiments the implant apparatus includes locking features to secure the surgical templates to the precision adjustable clamping device at the target bone area. In yet other embodiments the locking features secure the surgical template support platform of the surgical clamp in a fixed position at the target bone area. In further embodiments the self-limiting depth control features of all the surgical bone drills, guide pins, and component drivers are adapted so as to be used in conjunction with the self-limiting design features of the surgical templates secured into a surgical guide clamp at the target bone area. In yet other embodiments the surgical guide clamp incorporates features that allow for the easy and accurate repositioning of the surgical templates over another target bone area while the surgical guide clamp remains clamped over the initial target bone area. In additional embodiments the surgical guide clamp also allows for the securing of the surgical templates over a secondary target bone area.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein:

FIG. 1a is a front view of a vertical stacking of the components of one possible embodiment of a three-stage single-rooted implant of the improved implant 77 of the present invention;

FIG. 1b is a front view of a vertical stacking of the components of one possible embodiment of a two stage single-rooted implant of the improved implant 77 of the present invention;

FIG. 1c is a front view of a vertical stacking of the components of one possible embodiment of a three-stage multi-rooted implant of the improved implant 77 of the present invention;

FIG. 1d is a front view of a vertical stacking of the components of one possible embodiment of a two stage multi-rooted implant of the improved implant 77 of the present invention.

FIG. 2e is a bottom view of one possible embodiment of the "head" component 2 depicted in FIG. 2a;

FIG. 4a is top view of one possible embodiment of the surgical template precision support insert 17 of the present invention;

FIG. 4b is a top view of one possible embodiment of a primary surgical template 18 of the present invention;

FIG. 4c is a top view of one possible embodiment of a secondary surgical template 19 of the present invention;

FIG. 4d is an angled bottom view of one possible embodiment of the surgical template precision support insert 17 depicted in FIG. 4a;

FIG. 4e is an angled bottom view of one possible embodiment of the primary surgical template 18 depicted in FIG. 4b;

FIG. 4f is an angled bottom view of one possible embodiment of the secondary surgical template 19 depicted in FIG. 4c;

FIGS. 5a-5f are a series of angled top views of several possible embodiments of fully assembled single-rooted and multi-rooted implants of the improved implant 77 of the present invention;

FIGS. 5g-5k are a series of angled bottom views of the fully assembled single-rooted and multi-rooted implants depicted in FIGS. 5a-5f of the improved implant 77 of some embodiment of the present invention;

FIG. 7b is a close-up enlarged view of an embodiment of a segment of the free-standing precision surgical guide clamp 38 depicted in FIG. 7a;

FIG. 9b is an even closer-up angled side view of a segment of an embodiment of the precision surgical guide clamp 29 depicted in FIG. 6a;

FIG. 9c is an angled close-up view from the top perspective of an embodiment of a different segment of the precision surgical guide clamp 29 depicted in FIG. 6a;

FIG. 10a is an angled close-up view from the side perspective of an embodiment of a segment of the surgical template precision support platform 31 and more specifically of an embodiment of the platform precision adjustment element 51 depicted in FIG. 8a;

FIG. 10b illustrates an angled top view of the assembly (from left to right) of an embodiment of the parts needed to assemble the platform precision adjustment element 51 depicted in FIGS. 8a and 10a;

FIG. 15 depicts an angled top view of an embodiment of the driver assembly illustrated in FIG. 14 fully engaged within the secondary surgical template 19 of FIG. 14, and below that, the same surgical template 19 engaged within the precision guide clamp 29 depicted in FIG. 6a;

Figure 2A:
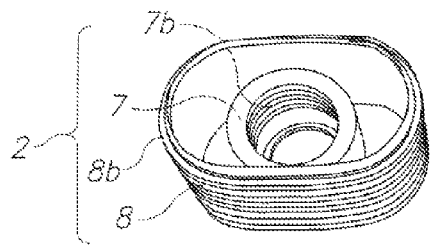
FIG. 2a is a top view of one possible embodiment of the "head" component 2 of a three-stage single-rooted implant of the improved implant 77 of an embodiment of the present invention.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

The word "stage" as used herein refers to the different overall types of separate sections of the implant. A "component" is a particular version (size, shape or number) of the parts of that type of distinct "stage" being used to assemble the different types of stages of the implant into one whole implant.

Non-limiting embodiments of the invention include improved systems, means and methods for the preparation and insertion of improved anatomically corrected implants that more closely imitate the overall natural form of the root system of human teeth. In some embodiments this system includes two detachable modular stages with customizable features to which a third abutment stage is attached or alternatively, is an integral part of one of the two stages.

The implant system, apparatus, tools, kit and methods of the present invention substantially solve many of the problems associated with the prior art. For example, a multiple "root screw" implant design would significantly increase the total bone to implant interface surface as compared to the current single "root screw" design, a significant biomechanical advantage as it would allow for vastly greater bone adhesion and "osseo-integration" of the improved implant.

Initial rigid fixation is desirable for osseo-integration to occur. This initial rigid fixation is enhanced by engaging the hard, dense cortical bony plates of the jawbones. An implant that would incorporate in its design a more naturally contoured cross-sectional dimension of the "head" of the implant may allow the dentist upon initial placement of the implant at the implant site to directly engage these cortical bony plates with the "head" segment, allowing for the immediate fixation of the implant in the bony implant site. This would represent a significant advantage over the prior art, both for cases where the dentist plans on "burying" the implant for an extended period of time in order to allow for osseo-integration prior to loading of the implant as well as in cases where the dentist intends to immediately load the implant. Immediate loading is a technique which has become more popular of the past few years as it allows the dentist to restore the missing tooth immediately, allowing for an immediate esthetic solution to the missing tooth.

In order to allow for a stable and durable implant form the diameter of the "root screw" component of the implants along its entire shaft must be of sufficient girth in order to provide the necessary support for the abutment and crown which sit atop it and the forces transmitted through them (when they are placed in function) to the implant "root" buried in the jawbone. Based on the above space limitations, it is determined that in order to accommodate multi-root screws in a healthy long term biological manner, this requires for these multiple "root screws" to be of a smaller diameter than the current single "root screw" design of standard implants.

In order to allow for the placement of a "multi-root" design implant into this very limited bone volume, one must consider all the described above limiting factors and balance them with the desire to place the largest diameter implant "roots" possible given these constraints, so as to allow for the placement of the most stable and durable "multi-root" implant into the implant site.

As noted above, the very limited three-dimensional volume of bone represents the implant site and presents severe challenges for the successful implantation of the standard "single root" implant design within it in a reproducible and safe manner. To achieve this goal successfully in order to provide for a stable and durable "multi-root" form implant for the posterior teeth that is able to withstand the considerable load forces it must endure both in the short and long term, represents an even greater challenge, one which requires the accurate and precise preparation of the implant site in a three-dimensional manner as well as the accurate and precise insertion of the implant components within this site in a three-dimensional manner. Any system, to be successful in achieving this goal, must incorporate features that allow for precisely this result.

The improved multi-root posterior implant of embodiments of the present invention not only splints together multiple implant "root screw" forms but does so endosseously (completely imbedded in bone). This means that the current invention is stronger, more stable and more durable than any of the standard posterior implant designs.

There is provided, in accordance with an embodiment of the present invention, an apparatus, system, and method for a modular design two or three-stage anatomical dental implant system, for supporting a fixed or fixed/removable dental prosthesis (i.e. individual crowns, multiple crowns, or over-dentures) comprising in the two stage embodiment, modular single and multiple distal "root screw" stage(s) or components which are attached to a modular customizable proximal "head/abutment" stage or; in the three stage embodiment, modular single and multiple distal "root screw" stage (s) or components which intimately fit into a modular customizable proximal "head" stage (component) of the improved dental implant into which in turn intimately fits a third abutment stage (component). These components allow for the assembly of improved single and/or multiple "root" dental implants for anterior and posterior teeth.

When the first two stages of the improved implant have been fixed into the patient's jawbone, this allows the dentist in the three-stage embodiment to intimately fit a third stage ready-made cast or castable abutment utilizing the anatomically formed "head" stage of the implant as its attachment. In the two-stage embodiment the "abutment" is an integral part of the "head/abutment" component. In both embodiments, the proximal "head" or "head/abutment" stage does not extend deeply into the bone, and the distal "root screw" stage (s) or components intimately fit into the "head" or "head/abutment" stage and are smaller or equal in overall dimension to standard dental implants, allowing for conservative bone preparation at the implant site. The "head" or "head/abutment" stage of the implant may also include in both embodiments a ready-made prosthetic crown margin interface extending above the crest of the jawbone at the cervical junction (cemento-enamel junction level) allowing for superior marginal integrity and seal of the fixed prosthesis (crown). In both embodiments, the "head" or "head/abutment" stage and "root screw" stages can be shaped to allow for the "root screw" stages to attach to the "head" or "head/abutment" stage either parallel to or angled in relation to each other. In both embodiments the "head" component or "head/abutment" component may include micro-grooves and ridges on its external surface for enhanced primary retention and subsequent bone adhesion. In the embodiment that is designed for over-dentures, a unique abutment design and unique adjustable over-denture bar design is described.

Furthermore, precision surgical guide tools and methods for the accurate, precise, and reproducible implantation of the two and three-stage improved dental implant system at the implant site designed specifically for the improved two and three-stage dental implant are also disclosed.

Embodiments of the present invention provides for an improved design of several types of dental implants (single-"rooted" anterior implants, and single and multi-"rooted" posterior implants) inserted into the alveolus of the upper and lower jaws as well as a set of precision surgical tools and a method of utilizing them for the accurate, precise and reproducible implantation of the improved dental implants described below. The improved implant(s) is/are comprised of two detachable and modular stages to which a third abutment stage is either connected to as a separate stage or is an integral part of one of these two stages. The first stage, the distal modular stage, is comprised of either single, a pair, or multiple cylindrical "root screw" forms or implant screws that may be tapered or straight along their length and that may have on their exterior surface rod-shaped, screw-shaped, and or having fins to assist in retention to the bony alveolus. These distal "root screw" stages will be made available in a kit of components of varying lengths and diameters, allowing the dentist to choose and "mix and match" on the same dental implant different sized implant "root screw" components for "multi-rooted" implants, and for both single and multi-"rooted" implants to choose from a kit of different sized and different form "head" or "head/abutment" components the one that provides the most advantageous composite of the two separate stages for any particular implant site. These "root screw(s)" components may attach either parallel to or angled to the "head" component and the root screws themselves may be parallel or offset from each other.

Criteria for choosing which composite of components are most advantageous to employ and assemble may include, but not be limited to, among other criteria, a diagnostic consideration of the anatomical limitations of the implant site as well as an evaluation of the requirements for anchorage and stability of the dental implant to be placed, based on the location and anticipated functional load the dental implant will be expected to bear.

The proximal detachable "head" or "head/abutment" stage of the implant in embodiments of the present invention, which is meant to replace the current integral "head" or top section of a standard implant, is shaped to conform more closely than all the previous state of the art to the natural cross-sectional form of the different types of roots of maxillary and mandibular (upper and lower jaw) teeth (incisors, cuspids, premolars and molars) at the level of the crestal ridge (the level of the cervix). The "head" components or "head/abutment" components of this stage are relatively shallow in their overall vertical dimension in order to allow for the conservative bone preparation at the implant site needed to accommodate its more natural cross-sectional form (oval, rhomboid, kidney-shaped, or other custom shape).

The two separate stages ("head" and "root screw") are intimately fitted and attached into each other via fitted sleeves and collars or other means of coupling including, but not limited to, internal threaded screw retention of the two stages in order to provide a tightly sealed coupling between the two stages and minimize any micro-gapping between them.

The "head" or "head/abutment" components in embodiments of the present invention incorporates single or multiple attachment points on its distal or inferior surface, allowing for the assembly of single, bi and tri-"rooted" implant forms with smaller or equal sized multiple "root screw" forms to replace the missing molar teeth while actually enhancing the stability and ability to withstand the loading force of functional and para-functional chewing or grinding. There is an additional distinct advantage as it allows several embodiments of the improved implants to be placed in locations that would previously not have allowed for the larger sized standard "single root" implant root forms to be placed in the alveolus without first subjecting the patient to additional surgical procedures such as maxillary sinus lifts or maxillary or mandibular ridge augmentation procedures. This saves the patient from the trauma of these surgeries, reduces healing time, and saves the dentist valuable treatment time and overall time required to complete each case. It also provides additional advantage as it allows for more conservative bone drilling at the implant site due to the fact that the dentist may choose to drill smaller sized "root screw" bore shafts in order to insert smaller dimensioned implant "root screw" components.

Additionally, since embodiments of the present invention also include "head" and "head/abutment" stages that allow for the connection of multiple "root screw" stages to the "head" or "connector" stage to form a "multi-rooted" implant, another significant advantage is that it provides enhanced structural advantages both in retention of the implant in the bony socket (s) and greater ability to withstand over time the forces and load of the natural "bite" and chewing, clenching, and grinding loads both in normal use and in patients who grind their teeth or clench their jaws (paranormal function) over the standard "single-root" implant.

Due to the far greater surface area of the improved implant that is buried in bone, the implant to bone interface is far greater than in any standard implant. This may result in improved healing time as well as providing for a greater amount of osseointegration for the implant and therefore greater "loading" capacity of the improved implant of the present invention over any standard "single-rooted" implant once healing is complete. This enhanced loading capacity of the improved implant is especially desirable when the dentist wishes to use several of the improved implants as the fixed support structure for a removable over-denture.

Additionally, embodiments of the present invention contain a three-stage embodiment wherein is incorporated in the inner aspect of the proximal "head" stage an internal connector or connectors, such as but not limited to, an internal threaded shaft machined to accept a separate third stage abutment segment comprising either a screw-in or snap-in abutment whose purpose is to act as the supporting structure for the implant crown to be fabricated by the dental practitioner. The more anatomically correct modified oval, elliptical, or rhomboid cross-sectional shape of the "head" or "head/abutment" component as well as the uniquely designed multi-point internal connectors of the "head" or "head/abutment" component to a third "abutment" component that fits precisely into it (hand in glove) and provides for superior anti-rotational features as well. This is due to the intimate frictional contact of the entire internal surface of the "head" or head/abutment" component to a large portion of the external surface of the "abutment" component as well as the frictional fit to significant internal surfaces of the abutment. This secure and completely rotation-free connection between the "head" stage of the improved implant and the "abutment" is a significant advantage of the present invention over the prior state of the art.

Additionally, in embodiments of the three stage design for anterior and posterior single "rooted" and posterior multi-"rooted" implants, a large portion of the abutment "sinks" into the extensive internal hollowed out ("basket") unique design of the separate "head" component (which is buried in the bone) and so allows for an advantageous distribution of the load forces not found in any of the prior art.

Additionally, embodiments of the present invention may contain an implementation wherein the outer border of the area referred in the dental literature as the "collar" or "margin" of the proximal "head" or "head/abutment" component is machined to provide an ideal 360 degree restorative margin for the dentist to fabricate the crown to be fitted upon the present embodiment implant form. This feature is incorporated to further enhance the seal and marginal integrity (prevent leaking or seepage) of the final restorative crown to the implant. The "head" or "head/abutment" component may also have an embodiment which incorporates "micro-threads" or smaller ridges and grooves on its external surfaces to increase its external surface area and: 1) maximizes bone adhesion to the "head" component; 2) minimize pathogenic microbial infiltration of the peri-implant (bone surrounding the implant) space; and 3) enhance the ability of the implant to achieve primary fixation by engaging the hard bony cortical plates of the jawbones, another distinct advantage of present invention over all the prior state of the art.

As the unique design of the surgical templates provided in embodiments of the present invention can be shaped in an infinite variety of shapes and dimensions, by varying the length of the "head" in this dimension allows for varying the distance between the "root screws" of a "multi-rooted"

implant as well. This allows for numerous biomechanical advantages over the known art as it allows for the increased retention, strength, and durability of the multi-root implant of the present invention over all the prior art, especially relevant in supporting an overdenture bar for a full removable denture (in the edentulous patient the mesio-distal dimension of the head can be substantially increased as there are no adjacent teeth to consider). Additionally, this particular design feature of the present invention allows for greater width of bone volume between the "root screw" components of the improved implant, a further biological advantage over the entire prior art.

Embodiments of the present invention also provide for a single "root screw" stage that attaches to an anatomically more correct (oval) anterior "head" or "head/abutment" stage for anterior dental implants as well as a single "root screw" stage that connects to a "head" or "head/abutment" stage for molar teeth where the mesio-distal bone volume width of the edentulous implant site does not allow for the placement of two "root screw" stages.

Embodiments of the present invention also provide for unique "abutment" components for an improved three stage single and multi-root implant shaped to intimately fit into the corresponding "head" components which contain uniquely designed (described in the drawings below) internal hollowed areas for the insertion of a novel new adjustable over-denture bar assembly with locking features. This intimate fit of the present invention's pre-cast overdenture bar assembly components to the abutment components of the implants provides for a more exact fit than the entire prior art, as the entire prior art relies on dental impressions and laboratory castings (which are known in the dental field to be inherently inaccurate due to the expansion and contraction of the materials involved in its fabrication) in order to fabricate the standard over-denture bar framework. When the improved overdenture bar assembly of the present invention is inserted into either the single or multi-root implants of the present invention, a full arch over-denture support may be prepared, assembled and inserted into the edentulous patient's mouth. This new design provides for greater retention, stability, strength, and durability of the implant-prosthesis over the entire prior art.

Embodiments of the present invention also provide for a unique two and three stage improved implant wherein the two stage design allows for the securing of two separate overdenture attachments to the "head/abutment" component or in the three stage design either two separate overdenture attachments to the separate abutment component or a unified double over-denture attachment which has a locking element to secure it to the separate abutment component.

Both the "head", "head/abutment" and "root screw" stages of embodiments of the present invention may be made of bio-compatible materials including, but not limited to, metal, ceramic, glasses, or any combination thereof, and potentially having various coatings of materials such as titanium beads, titanium plasma spray, hydroxyapetite, or bone growth chemicals or similar coatings to enhance attachment to bone.

To simplify, standardize, and allow for consistent and precise reproducibility of insertion, the following embodiments of novel surgical devices may be employed to prepare the bony alveolus site (osteotomy) to accept the present invention implant forms:

A kit of different sized primary self-limiting (in all three dimensions) surgical templates (either re-usable or one-time use) which are slightly larger in dimension but exactly corresponding to the cross-sectional shape of the different "head" or "head/abutment" stages at the level of the bony crest height (level of the cervix) as will be illustrated in the drawings below. The dental practitioner chooses the most appropriate shape and size template from the kit and secures it in a precise location via the precision adjustable clamping device described below over the implant site to act as a drill guide form for the bone preparation of the "head" component of the three-stage implant design or the "head/abutment" component of the two-stage implant design of the present invention. These self-limiting primary surgical templates allow for the precise shape, depth, levelness of the floor, and accurate location of the top portion of the bone preparation (osteotomy) in relation to the adjacent teeth, or in the edentulous patient, to the exact jaw location deemed most advantageous by the dental practitioner for the placement of the implant.

A kit of different sized self-limiting (in all three dimensions) secondary surgical templates (reusable or one-time use) corresponding in dimension (though possibly slightly larger) to the dimensions of the actual "head" or "head/abutment" stage implant form and corresponding to the primary surgical template form it is designed to be used with. These secondary surgical templates include in their design self-limiting drill guide holes to properly drill the "root screw" bone shafts in the bone at the implant site at the proper angulations, position, and depth in relation to the bone preparation at the implant site for the "head" or "head/abutment" stage that has already been prepared. These secondary surgical templates also act as accurate depth gauges to initially check both the depth and levelness of the floor of the initial bone preparation (osteotomy) of the "head" or "head/abutment" stages. These same surgical templates utilize these self-limiting insertion guide holes to:

a. check for the angulations (parallelism) and location of these bore shafts in relation to the adjacent teeth when utilized in conjunction with the self-limiting surgical guide pins that are specifically designed for use with the secondary surgical template.

b. insert the "root screw" stage components of the improved implant of the current invention in the proper location and to the exact proper vertical depth within the bore shaft(s) when utilized in conjunction with the self-limiting "root screw" driver specifically designed for use with the secondary surgical template.

c. properly relate the "head" stage component of the improved implant of the current invention and allow for the intimate connection of the two stages to each other via either the connector screws provided for the attachment of the two stages to each other or some other means of connection.

A precision adjustable clamping device of various different designs is also provided for in embodiments of the present invention. One embodiment, which may be used even in the completely edentulous patient clamps directly into the concave undercuts of the gingival vestibules of the oral cavity while another variant of this embodiment allows for the temporary rigid fixation of this same clamp in these same vestibules after reflection of the gingival tissue via fixation screws or other fixation elements. An entirely different embodiment of the clamping device clamps directly to a natural tooth or teeth adjacent to the implant site. These clamps act as a fully adjustable (in all three dimensions and is even rotatable) support and fixation platform to secure both the primary and secondary surgical templates described above accurately, precisely and intimately over the implant site of both the upper and lower jaws as will be illustrated in the drawings below. These surgical implant tools both simplify and standardize the bony preparation of the implant site by providing an accurate three dimensional self-limiting guide when used in conjunction with the self-limiting dental implant drills and implant guide pins of the present invention (described below)

in order to prepare the implant site in a three dimensional manner to receive the improved implant of the present invention as well as allowing for the accurate and precise assembly of the implant components of the two and three-stage improved implants of the current invention in a three dimensional manner within the limited bone volume of the implant site.

A kit of self-limiting dental implant drills, implant guide pins, implant component and implant screw drivers specifically designed to be used in conjunction with the surgical templates and surgical clamps of embodiments of the present invention in order to properly prepare the alveolus (osteotomy) for the insertion of the improved two and three-stage dental implants of the present invention.

Relation of Embodiments of the Present Invention to Aspects of Known Art:

For example, in relating to U.S. Pat. No. 6,854,972, the cross-sectional form described at the superior aspect of the "head" of the implant remains round in form and so does not reflect the natural more oval cross-sectional form of the natural anterior teeth at this level (CEJ). Since the "head" portion is an integral part of the one piece main body, it offers none of the advantages of the modular separate "head" or "head/abutment" design of the present invention. This modular design of these two stages in the present invention allows the dentist to place a more naturally shaped "head", a distinct biological advantage, as well as the freedom to assemble the most advantageous composite of these two stages for any particular implant site based on many important criteria, such as, but not limited to the volume of bone present, the quality of bone at the implant site, and esthetic considerations.

Relating to U.S. Pat. No. 6,093,023, the polygonal abutment described contains none of the advantages of the modular natural shaped "head" or "head/abutment" components of the present invention which are placed endosseously (in the bone).

In relating to U.S. Pat. No. 7,291,013, the suggested implant configuration still maintains a round cross-sectional form of the integral head of the "single-root" implant, and therefore does not incorporate the advantages of the present invention's anterior "single-root" improved implant.

Relating to U.S. Pat. No. 6,527,554, the implant type described offers some improvements on prior implants, yet still maintains a round cross-sectional form and offers none of the advantages listed below of the present invention. Additionally, the improved implant of the present invention utilizes micro-threads and grooves to achieve the same result in a more profound way while also significantly enhancing the retentive qualities of the implant to a much greater degree than does this prior art.

In relating to U.S. Pat. App. No. US 2010/0003638 describes an implant design with additional suggested improvements, however this implant maintains the round cross-sectional form of its modular "head" segment, it does not offer the biomechanical, biological and esthetic advantages of form of the more naturally shaped modular "head" design of the "single-root" embodiment of the present invention.

Relating to WO Pat. App. No. 2006/082610 describes an implant design with a "head" component which it calls a "collar" and a "root screw" component which it calls a "fixture". The multi-root implants it describes are three-stage only in their design and do not include the two-stage design embodiment of the present invention. They are also only designed to replace "multiple-root" posterior teeth, while the design of the present invention also allows for the replacement of "single-root" and "multiple-root" posterior teeth as well as "single-root" anterior teeth.

Relating again to WO Pat. App. No. 2006/082610 further contains a minimal internal hollowed out area in its "head" stage for the intimate insertion of the "abutment" stage. In the present invention, the internal hollowed out area of the "head" component is extensive, encompassing the entire inner surface area of the "head" component. This extensive internal hollowed feature of the present invention, by providing for a more intimate fit of these two components in a "hand in glove" manner, also provides for far greater frictional fit and so greater anti-rotational function as well as wider and more uniform distribution of the forces of mastication or "load" over the entire structure of the improved implant compared to this prior art once the implant is placed in full function with a crown placed on it. Due to the intense load and off-axis (shear) force component of that load (noted above) placed on posterior dental implants in full function during normal chewing and paranormal grinding by the patient, (particularly on the "multi-rooted" posterior molars) an improved implant design, such as is described in the present invention, that allows for just such a wider and more uniform load distribution throughout the structure of the entire implant, represents a major advantage over all the prior art.

Additionally, as opposed to some embodiments of the present invention where a three-stage multi-root embodiment is used, WO Pat. No. 2006/082610 does not contain an internal screw collar or ring feature projecting up from the top surface of its "head" component to further increase the frictional fit between the "head" stage and the "abutment" stage. The prior art thus relies to a much greater degree on the single set of two "connector" screws between all three stages of these components (abutment, head, and two root screws) to achieve a solid and secure connection between all of these components. This design is highly undesirable as it places undo forces on this single pair of "connector" screws which over time may loosen or fracture, causing either failure of the crown, or more seriously, failure of the implant. In the present invention, due to its unique "hand in glove" design of the "head" and "abutment" stages, which, as noted above, also includes a large surface screw collar (s) or ring (s) feature projecting upward from its internal surface of the "head" component as well as the two separate pairs of connector screws as also noted above, there is a much reduced reliance on each individual pair of "connector" screws to achieve an intimate and secure connection between these stages, another significant improvement in design over all the prior art.

Further, as opposed to some embodiments of the present invention, WO Pat. No. 2006/082610 also does not incorporate micro-threads or grooves on the surface of its "head" component for the enhancement of the adhesion of bone to this critically important component, as this component is the most proximal component of the implant and so is closest to the oral cavity and the numerous pathogenic microbes contained within it. By enhancing bone adhesion in the initial stages of healing and subsequently thereafter for the long term, these micro-threads on the "head" stage of the present invention help to prevent the infiltration of these pathogenic bacteria into the coronal segment of the implant, preserving bone and increasing the longevity of the implant in the mouth. These same micro-threads act to enhance primary fixation of the improved implant, a highly desirable result as it may allow for the immediate "loading" of the implant, so that the patient can actually use the temporary crown placed on it immediately.

In further relating to WO Pat. No. 2006/082610, embodiments of the present invention incorporate in their design indented (concave) collars or rings on the underside surface of the "head" or "head/abutment" component to which is related in an intimate manner (from below) the superior aspects of the "root screws". In the improved implant of the present invention the "root screws" do not need to be threaded through the retention holes of the "head" component in order to engage with the "head" component as in the prior art. This novel design of the present invention allows for the "root screw" components to be of significantly greater diameter than the retention hole of the "head" or "head/abutment" component and of significantly larger diameter than the "root screws" of the prior art.

This design feature of the "head" component of the present invention, apart from providing an intimate and positive seat of the "root screw" components to the underside of the "head" component also acts to prevent "micro-gapping" between these two components and so prevents the possible infiltration of pathogenic bacteria between them, a further advantage of the design of the present invention. As noted above, the novel physical relation and sequence of relation of these components to each other also allows for the use of significantly larger diameter connector screws than the prior art (since the root screws are of greater diameter, the connector screws can be of greater diameter as well). These connector screws are of sufficient diameter (girth) to withstand the load forces (including shear forces) placed upon the improved dental implant for the long term, and so provide for a robust and secure connection of these components over the long term, a major advantage over the prior art, and an absolute requirement that allows the dentist to place with confidence the improved multi-root implants of the present invention in the posterior areas of the jawbones without fear of these implants fracturing under long term loading.

Another major drawback in the design of the prior art relates to the fact that as mentioned above, it employs only one set of two connector screws to secure all three stages of its components (abutment, head and two root screws) to each other with no stress breaking feature between them.

The improved implant of the present invention both in its two and three-stage embodiments solves all of the above drawbacks in design of the prior art by allowing for the placement of two sets of two connector screws (in the bi-rooted embodiment). One set of two connector screws of sufficient diameters actively secure the "head" or "head/abutment" component to the two "root screw" components of sufficient diameters at the initial insertion of these components into the implant site. This prevents the possibility of any shifting between these components during the extensive healing phase. The other set of two connector screws actively secure the "abutment" to the "head" component after healing in the three-stage embodiment of the present invention or simply secure the access shaft of the "head/abutment" component in the two-stage embodiment of the present invention.

By utilizing two sets of two connector screws, a stress breaker feature is thereby incorporated into the structural design, another advantage of embodiments of the present invention over the know art.

In relating to U.S. Pat. App. No. US 2010/003635, the implant design described contains none of the modular design advantages of embodiments of the present invention, and utilizes a non-standard material composition that is less retentive as it contains no threads in its "root" design to bite into the surrounding jawbone or allow for the intimate adhesion of the surrounding bone during the osseointegration phase of healing.

Relating to U.S. Pat. App. No 2008/0293012, the splint abutment component described offers none of the biomechanical advantages of present invention as it utilizes the standard cylindrical "root" form of standard two stage dental implants implanted in the jawbone into which it connects a wide platform abutment component which sits above the height of the crestal jawbone in the mouth and to which is connected the crown that the patient chews with.

The present invention in its "single-root" design embodiment (two and three stage) for posterior teeth incorporates an anatomically correct "head" which is inserted and embedded in the jawbone (endosseous). The abutment component of the improved implant of the present invention which connects into the "head" component in its three-stage embodiment, does so in an intimate "hand in glove" manner, providing for the proper distribution of the biting forces over the entire structure of the implant, a distinct advantage over all the prior art, and particularly over the disadvantageous biomechanical design of U.S. Pat. No. 2008/0293012 described above, while providing the proper "root" form for a posterior (molar) implant abutment. In the two-stage embodiment of the "single-root" posterior improved implant of the present invention, the abutment component is an integral part of the "head/abutment" component and so also provides for the proper distribution of loading forces on the entire implant.

Relating to U.S. App. Pat. No. US2004/0013999 and U.S. Pat. No. US2009/0202959, the surgical guide clamps described do not allow for the preparation of the modular design and differently shaped separate "head" and "root screw" forms (components) of the present invention. Additionally, this prior art's ring guide also does not allow for the preparation of the bone at the implant site to receive separate and differently shaped forms (components) of the "head" and "root screw" stages of the present invention and is limited to preparing a standard implant form whose head is round in cross-section and of the same diameter as the rest of the implant. Additionally, the known art does not describe a freestanding embodiment of its guide clamp (not clamped to the teeth) as do some embodiments of the present invention.

A further major drawback of the entire prior art (including WO Pat. No. 2006/082610) is that they do not allow for surgical templates that allow for the placement of different mesio-distal length "heads". As the unique design of the surgical templates provided in the present invention can be shaped in an infinite variety of shapes and dimensions, varying the length of the "head" in this dimension allows for varying the distance between the "root screw" components of a "multi-rooted" implant as well. This allows for numerous biomechanical advantages over all the prior art as it allows for the increased retention, strength, durability of the multi-root implant of the present invention over all the prior art, especially relevant in supporting an overdenture bar for a full removable denture (in the edentulous patient the mesio-distal dimension of the head can be substantially increased as there are no adjacent teeth to consider). Additionally, this particular design feature of the present invention allows for greater width of bone volume between the "root screw" components of the improved implant, a further biological advantage over the known art.

Regarding the prior art usage of standard implants with their single "root screw" design, in order to allow for a stable and durable implant form, the diameter of the implants along their entire shaft must be of sufficient girth in order to provide the necessary support for the abutment and crown which sit atop them and the forces transmitted through them (when they are placed in function) to the implant "root"(s) buried in the jawbone. Based on the above space limitations, it is obvious that in order to accommodate multi-root screws in a healthy long term biological manner, requires for these multiple "root screws" to be of a smaller diameter than the current single "root screw" design of standard implants.

In the prior art WO 2006/082610 described above, the basic template described is utilized to drill the bore shafts (for the "root screws") of the osteotomy first. Next the more shallow and wider top portion of the osteotomy is drilled out (for the "head") utilizing the same basic template. The "head" component is then placed first into the upper portion of the osteotomy and the "root screw" components are then inserted into the "head" by sliding them through the small holes contained within the "head" component and threading them into the bore shafts.

In various embodiments of the present invention, the entire above sequence is exactly reversed. The primary surgical template is utilized to drill out the top portion of the osteotomy first (for the "head" component). The secondary surgical template is then placed inside the top portion of the osteotomy and utilized to drill the bore shafts of the osteotomy (for the "root screw" components). The secondary surgical template is then used to check the parallelism of the bore shafts with the adjacent teeth and then utilized to insert the "root screw" components first into the osteotomy. The "head" component is then fitted down onto the "root screws" and secured in the top portion of the osteotomy to the "root screw" components already in place below it via connector screws threaded through the retention holes of the "head" or "head/abutment" component.

By necessity there is an obvious direct relation between the tools and method used to prepare the implant site for the implant's insertion and the design form of the implant to be placed within this site. In layman's terms, the "peg" must fit the "hole". In the dental field, this fit must also be precise and reproducible in an easy manner by the dental practitioner in order to be able to achieve a high rate of success. More specifically, in the case of a multi-root implant for posterior teeth, in order to relate and assemble the components of the different stages in a three dimensional manner (along all three axes) in an accurate and precise manner within the bone preparation (osteotomy) it is of critical importance to relate the bone preparation for the "head" component with the bone shaft preparations for the "root screw" components. The prior art does not describe any design element incorporated into either the bone drills or the template it describes that would allow for a self-limiting depth (axis) control feature.

If the dentist errs in drilling by, for example, less than half a millimeter in the vertical depth (axis) of either of these two separate bone preparations, it will be impossible to insert the multiple components of the implant in a precise three dimensional manner. To make matters worse, this prior art (WO 2006/082610) does mention a small thin locking pin to be inserted into the body of the template but does not describe how one could possibly use this feature to fix the template securely in the implant site utilizing this feature in the center of the bloody implant site. It also provides no means of precisely relating the position of the template to the adjacent teeth, making the practical use of this template at the implant site very problematic.

Embodiments of the present invention do allow for just such a precise, accurate, and easily reproducible preparation of the entire osteotomy (head and root screw bone preparation segments of the osteotomy) in a three dimensional manner (as will be described in detail below) and the precise, accurate, and easily reproducible assembly of the components of the improved multi-root implant in a three dimensional manner (along all three axes) into the osteotomy, utilizing the surgical guide clamps, primary and secondary self-limiting surgical templates, and the self-limiting bone drills provided in the improved implant system of the present invention, another distinct advantage over the known art.

Embodiments of the present invention also provides for a robust, stable, and durable design of its components (root screw components and connector screws of sufficient diameter to withstand the load forces on molars, head components shaped to imitate the top root portion of the natural dentition, and abutment components which "sink" into the head component for a secure fit and proper distribution of the load forces) which should provide in the short and long term a solid multi-root molar implant the dental practitioner can rely upon and feel confident in placing in the patient's mouth over the long term.

The implant system design of the present invention allows the dentist to prepare, utilizing a kit of different shaped primary surgical templates, virtually any "head" or "head/abutment" stage bone preparation (osteotomy) he desires for the accurate placement of an almost infinite variety of "head" or "head/abutment" stage components (limited only by the number of forms provided in the kit) into any particular implant site for both "single" and "multiple" rooted implants, a very important feature based on the variability of bone volume and bone quality noted above, of the implant site from patient to patient and from site to site in each patient. This is a feature unique to the present invention and not provided for by the known art.

Reference is now made to FIG. 1a which is a front view of a vertical stacking of the components of one possible embodiment of a three-stage single-rooted implant of the improved implant 77 of the present invention. As can be seen in FIG. 1a, a single root screw component 1 is shown, as well as a head component 2, a screw connector 4 which secures the root screw 1 in an intimate fashion to the head 2. Also depicted is the abutment screw 5, which secures the abutment component 3 to the head 2 in an intimate manner.

FIG. 1b is a front view of a vertical stacking of the components of one possible embodiment of a two stage single-rooted implant of the improved implant 77 of the present invention wherein are depicted the root screw 1, secured via the connector screw 4 in an intimate manner to the "head/abutment" component 6. Additionally, an optional abutment screw 5 screws into the head/abutment 6 in order to securely seal the single access shaft 15 of the head/abutment 6.

FIG. 1c is a front view of a vertical stacking of the components of one possible embodiment of a three-stage multi-rooted implant of the improved implant 77 of the present invention wherein are depicted two root screws 1 which are secured in an intimate manner to the head 2 via two connector screws 4. Additionally, an abutment 3 is secured in an intimate manner to the head 2 via two abutment screws 5.

FIG. 1d is a front view of a vertical stacking of the components of one possible embodiment of a two stage multi-rooted implant of the improved implant 77 of the present invention wherein are depicted two root screws 1 which are secured to a head/abutment 6 in an intimate fashion via two screw connectors 4. Additionally, optional two abutment screws may be screwed into the two access shafts 14 of the head/abutment 6 to securely seal them.

FIG. 2a is a top view of one possible embodiment of the "head" component 2 of a three-stage single-rooted implant of the improved implant 77 of the present invention wherein is depicted the internal connecting ring 7 to provide for a more frictional fit of the head 2 to the abutment 3 and which is threaded 7b in order to accept the abutment screw 5. The superior lip of the head 2 has a beveled edge 8b. The outer side walls 8 of the head 2 may be micro-grooved 8a for added initial fixation properties of the head 2, to increase bone adhesion to the head 2, and to prevent microbial infiltration from the oral environment.

Figure 2B:
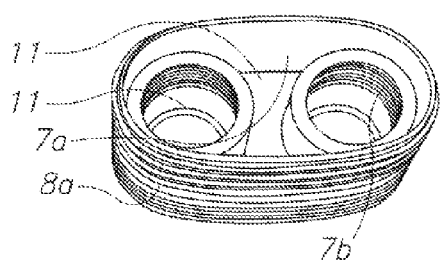
FIG. 2b is a top view of the "head" component 2 of one possible embodiment of a three-stage multi-rooted implant of the improved implant 77 of an embodiment of the present invention.

FIG. 2b is a top view of the "head" component 2 of one possible embodiment of a three-stage multi-rooted implant of the improved implant 77 of the present invention wherein are depicted a self-limiting circumferential flange 7a of the head component 2 which acts as a stop for the connector screws 4 and allow for the secure and intimate connection of the head 2 to the root screws 1. The head 2 has a floor 11 and internal side walls 9 which together with the internal connecting rings create a significant internal hollowed out area for the intimate and frictional fit of the abutment 3 within it.

Figure 2C:
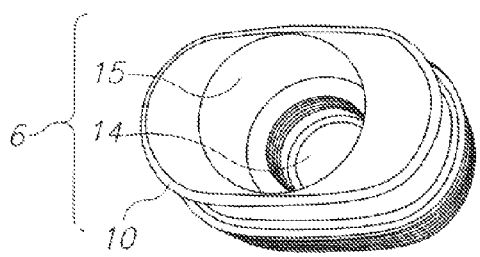
FIG. 2c is a top view of one possible embodiment of the "head/abutment" component 6 of a two stage single-rooted implant of the improved implant 77 of an embodiment of the present invention.

FIG. 2c is a top view of one possible embodiment of the "head/abutment" component 6 of a two stage single-rooted implant of the improved implant 77 of the present invention wherein is depicted the beveled edge 10 of the head/abutment component 6, the access shaft 15, and the connector hole 14 which allows for the connector screws to be inserted through them and into the root screw 1.

Figure 2D:
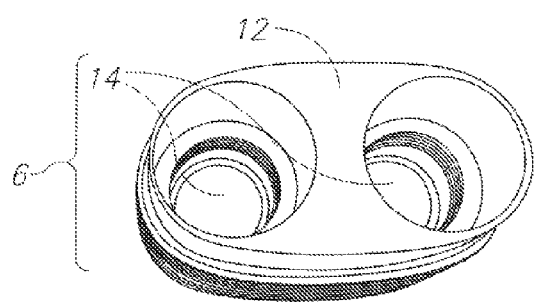
FIG. 2d is a top is a top view of one possible embodiment of the "head/abutment" component 6 of a two stage multi-rooted implant of the improved implant 77 of an embodiment of the present invention.

FIG. 2d is a top is a top view of one possible embodiment of the "head/abutment" component 6 of a two stage multi-rooted implant of the improved implant 77 of the present invention wherein is depicted one possible embodiment of the head/abutment 6 of the improved multi-root implant 77 of the present invention. Additionally, two connector holes 14, and a superior aspect support floor 12 for the crown are also depicted.

Figure 2E:
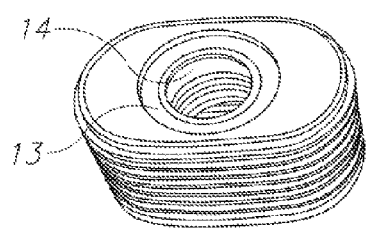

FIG. 2e is a bottom view of one possible embodiment of the "head" component 2 depicted in FIG. 2a wherein are depicted a connector hole 14 and one possible embodiment of a concave set ring 13 which allows for an positive, accurate, and intimate seat of the superior aspect 1a of the root screw 1 into the inferior undersurface of the head 2.

Figure 2F:
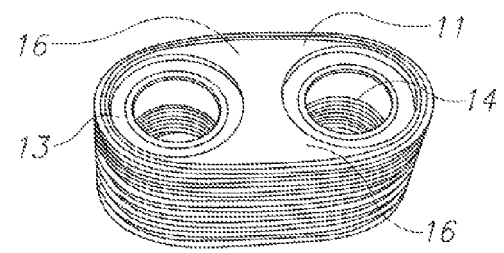
FIG. 2f is a bottom view of one possible embodiment of the "head" component 2 depicted in FIG. 2b.

FIG. 2f is a bottom view of one possible embodiment of the "head" component 2 depicted in FIG. 2b wherein are depicted two set rings 13, relevant dimensional markings 16 for easy recognition by the dental practitioner, and an underside surface 11 of the multi-root head 2.

Figure 2G:
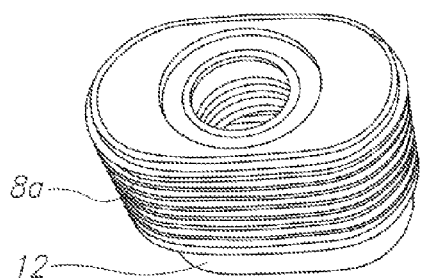
FIG. 2g is a bottom view of one possible embodiment of the "head/abutment" component 6 depicted in FIG. 2c.

FIG. 2g is a bottom view of one possible embodiment of the "head/abutment" component 6 depicted in FIG. 2c wherein is depicted one possible embodiment of micro-grooves or threads 8a of the exterior side walls 8 of the head component 2.

Figure 2H:
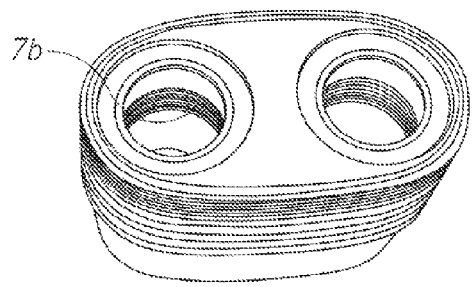
FIG. 2h is a bottom view of one possible embodiment of the "head/abutment" component 6 depicted in FIG. 2d.

FIG. 2h is a bottom view of one possible embodiment of the "head/abutment" component 6 depicted in FIG. 2d wherein is depicted the internal threads for securing the abutment screws 5 into the head 2.

Figures 3A, 3B:
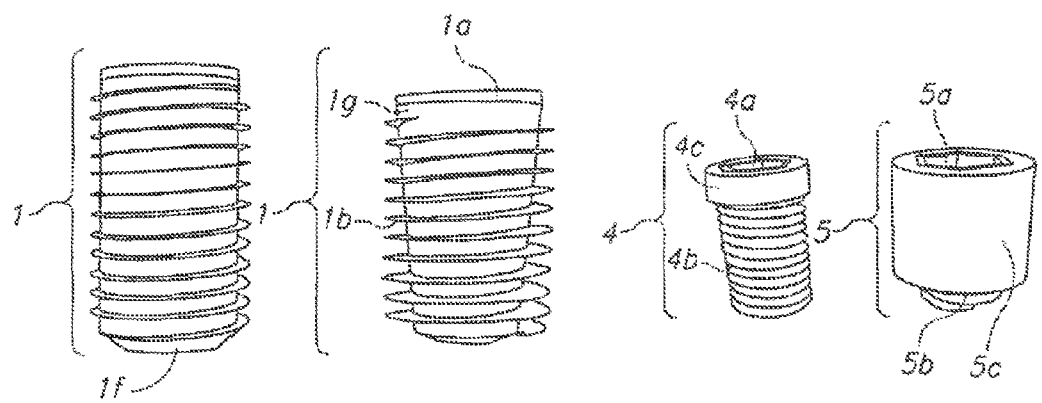
FIG. 3a is a front view of two possible embodiments of the "root screw" components 1 of the improved implant 77 of the present invention.
FIG. 3b is a front of one possible embodiment of a connector screw 4 and one possible embodiment of an abutment screw 5 of the improved implant 77 of the present invention.

FIG. 3a is a front view of two possible embodiments of the "root screw" components 1 of the improved implant 77 of the present invention wherein are depicted a straight profile and tapered profile root screw 1 with a non-threaded superior aspect 1a, exterior side walls 1g, and one possible embodiment of threads 1b.

FIG. 3b is a front of one possible embodiment of a connector screw 4 and one possible embodiment of an abutment screw 5 of the improved implant 77 of the present invention wherein the connector screw has a head 4c with a concave depression in the head's superior aspect surface 4a to accept a driver and a body with threads 4b. An embodiment of an abutment screw 5 is also depicted with a head section 5c, a concave depression in the head's superior aspect 5a to accept a driver, and a threaded body 5b.

Figure 3C:
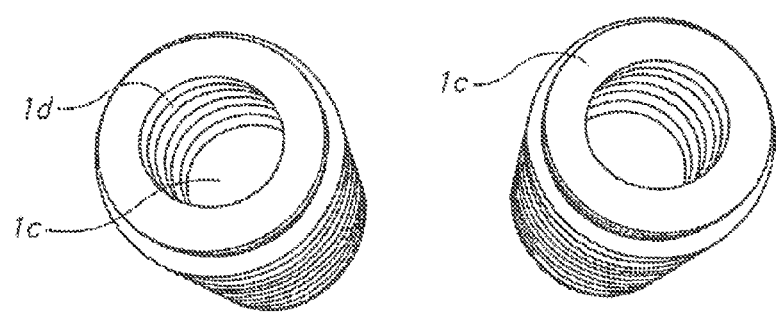
FIG. 3c is an angled top view illustrating two possible embodiments of the "root screw" components 1 of the improved implant 77 of the present invention.

FIG. 3c is an angled top view illustrating two possible embodiments of the "root screw" components 1 of the improved implant 77 of the present invention wherein are depicted the outer collar 1e of the superior aspect of its body, an inner machined cylindrical sleeve 1c with threads 1d to accept and allow for securing the connector screw 4 into its form.

Figure 3D:
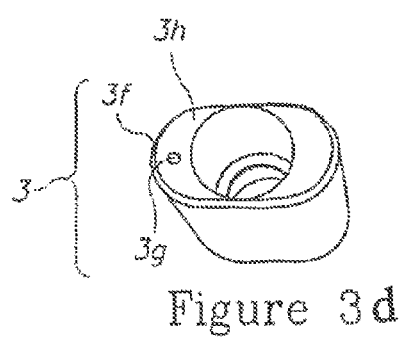
FIG. 3d is an angled top view of one possible embodiment of the abutment component 3 of a three-stage single-rooted implant of the improved implant 77 of the present invention.

FIG. 3d is an angled top view of one possible embodiment of the abutment component 3 of a three-stage single-rooted implant of the improved implant 77 of the present invention wherein are depicted an orientation marker 3g on its top surface 3h and a beveled edge 3f to its top surface 3h.

Figure 3E:
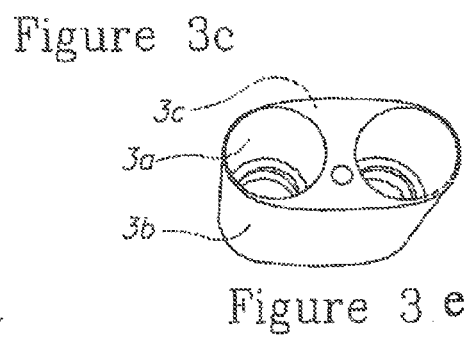
FIG. 3e is an angled top view of one possible embodiment of the abutment component 3 of a three-stage multi-rooted implant of the improved implant 77 of the present invention.

FIG. 3e is an angled top view of one possible embodiment of the abutment component 3 of a three-stage multi-rooted implant of the improved implant 77 of the present invention wherein are depicted a top surface 3c of the abutment 3, internal side walls 3a of the access shaft 3i for engagement with and frictional fit to the internal connective ring 7 of the head component 2, outer perpendicular sides walls 3b for engagement to and added frictional fit to the perpendicular internal side walls 9 of the head component 2. This design allows for a superior anti-rotational fit while maximizes the frictional fit between the head component 2 and the separate abutment component 3 of the three-stage embodiment of the improved implant 77 of the present invention. This "hand in glove" fit also translates into reduced reliance and stress on the connector screw (s) 4 to secure these two components to each other.

Figure 3F:
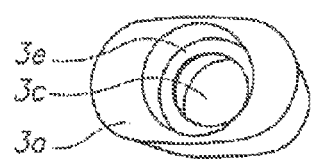
FIG. 3f is an angled bottom view of one possible embodiment of the abutment component 3 depicted in FIG. 3d.

FIG. 3f is an angled bottom view of one possible embodiment of the abutment component 3 depicted in FIG. 3d wherein are depicted the access shaft 3i, a circumferential internal limiting flange 3e for the head 5c of the abutment screw 5 to engage, and a flat bottom surface 3d which sits in an intimate manner onto the inner flat floor surface 11 of the head component 2.

Figure 3G:
FIG. 3g is an angled bottom view of one possible embodiment of the abutment component 3 depicted in FIG. 3e.

FIG. 3g is an angled bottom view of one possible embodiment of the abutment component 3 depicted in FIG. 3e wherein are depicted two circumferential internal limiting flanges 3e for the head 5c of two abutment screws 5 to engage, and a flat bottom surface 3h.

FIG. 4a is top view of one possible embodiment of the surgical template precision support insert 17 of the present invention wherein are depicted one possible embodiment of the template access hole 17a, a possible embodiment of two securing sleeves 21 to secure the surgical template precision support insert 17 to the surgical template precision support platform 31, and possible embodiments of template orientations pegs 20 to orient and secure the primary 18 and secondary 19 surgical templates to the surgical template precision support insert 17.

FIG. 4b is a top view of one possible embodiment of a primary surgical template 18 of the present invention wherein are depicted the "head" component 2's bone preparation form 22 which allows for the accurate and easily reproducible preparation of the bone to accept the insertion of the cross-sectional shape of the head component 2. Also depicted is the circumferential template limiting flange 25 which rests on the top surface of the surgical template precision support insert 17 and acts as well as a self-limiting feature for the self-limiting primary bone drill 61 in order to accurately control the depth of the osteotomy head preparation 71, the resultant level floor of the head preparation 71a and the perpendicularly straight side walls 71b of the head preparation 71. Additionally, one possible embodiment of template securing rings 20a are depicted within the template limiting flange 25 which are used to orient and engage the primary surgical template 18 onto the surgical template precision support insert 17.

FIG. 4c is a top view of one possible embodiment of a secondary surgical template 19 of the present invention wherein are depicted one possible embodiment of two of the self-limiting template access shafts 24 for the insertion of the rotary surgical tools and guide pins 64 for the accurate (along all three axes) preparation of the bone shafts 74 of the osteotomy in relation to the head preparation 71 and the accurate insertion of the root screw(s) 1 and the head 2 or head/abutment component 6 into the final osteotomy 73 and the precise relation of these components to each other within the final osteotomy 73.

FIG. 4*d* is an angled bottom view of one possible embodiment of the surgical template precision support insert 17 depicted in FIG. 4*a* wherein is depicted the bottom surface 17*b* of the surgical template precision support insert 17.

FIG. 4*e* is an angled bottom view of one possible embodiment of the primary surgical template 18 depicted in FIG. 4*b* wherein is depicted the extending circumferential flange 23 of the primary surgical template 18.

FIG. 4*f* is an angled bottom view of one possible embodiment of the secondary surgical template 19 depicted in FIG. 4*c* wherein are depicted the underside surface of the template limiting flange 25, the flat bottom surface 27 of the secondary surgical template 19 which acts as a depth gauge to check the depth and levelness of the floor of the head preparation 71, and the flat perpendicular side walls 26 of the secondary surgical template 19 to check the preparation of the internal side walls 71*b* of the head preparation 71 of the osteotomy.

FIGS. 5*a*-5*f* are a series of angled top views of several possible embodiments of fully assembled single-rooted and multi-rooted implants of the improved implant 77 of the present invention wherein is depicted one possible embodiment of an over-denture form abutment 28 in FIGS. 5*e* and 5*f*.

FIGS. 5*g*-5*k* are a series of angled bottom views of the fully assembled single-rooted and multi-rooted implants depicted in FIGS. 5*a*-5*f* of the improved implant 77 of embodiments of the present invention wherein are depicted an example of one possible difference in distance between the root screws 1 depending on the different dimensioned head component 2 to which they are assembled.

Figure 6A:
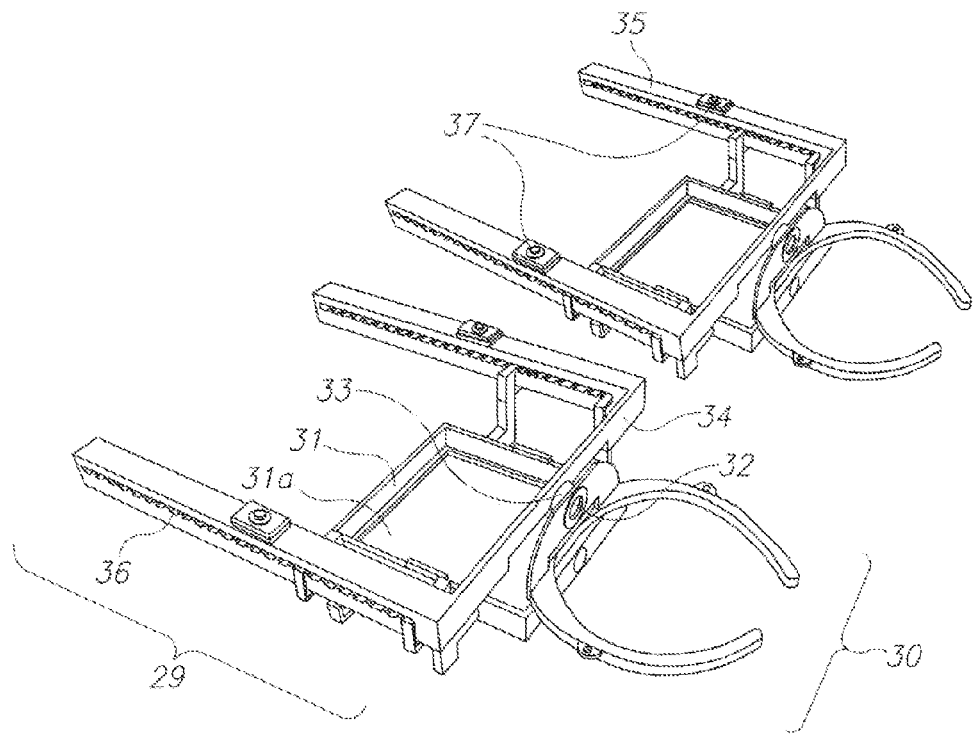
FIG. 6a is an angled top and side view of two possible embodiments of a precision surgical guide clamp 29 of the present invention that clamp on to a tooth or teeth in the jawbone to securely and accurately position the surgical templates 18 and 19 over the implant site.

FIG. 6*a* is an angled top and side view of two possible embodiments of a precision surgical guide clamp 29 of the present invention that clamps on to a tooth or teeth in the jawbone to securely and accurately position the surgical templates 18 and 19 over the implant site wherein is depicted two possible embodiments of the detachable clamp heads 30, an embodiment of the ratcheted internal rails 35 with its notched segments 36 for accurately positioning the surgical templates 18 and 19 over the implant site, an embodiment of the surgical template precision support platform 31 and its center cut-out 31*a*. Also depicted is the cross-beam element 34 which connects to the ratcheted internal rails 35 and which contains the swivel ball joint 33 for the off-axis orientation of the surgical templates 18 and 19 at the implant site and the attachment of the various detachable clamp heads 30 to the body of the precision surgical guide clamp 29.

Figure 6B:
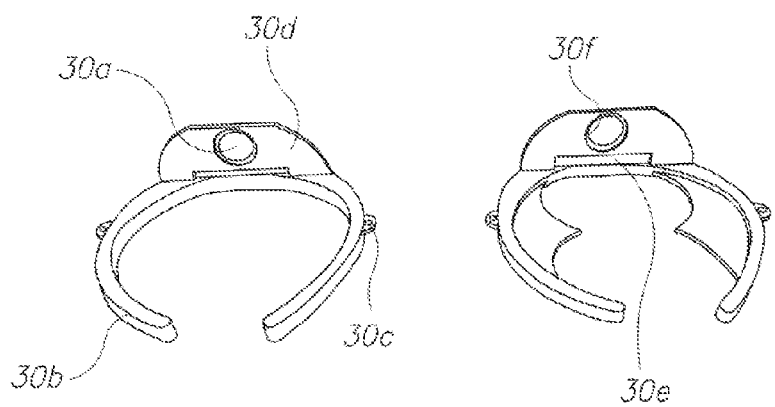
FIG. 6b is a close-up enlarged view from the top and front perspective of two possible embodiments of detachable clamp heads 30 of the present invention.

FIG. 6*b* is a close-up enlarged view from the top and front perspective of two possible embodiments of detachable clamp heads 30 of the present invention wherein are depicted the clamp head screw hole 30*a* and its circumferential limiting flange 30*f*, clamp arms 30*b*, spreader wings 30*c*, perpendicular support member 30*d*, and internal slot 30*e* within the perpendicular support member 30*d* to allow for the unencumbered rotation of the primary bone drill within the precision surgical guide clamp.

Figure 7A:
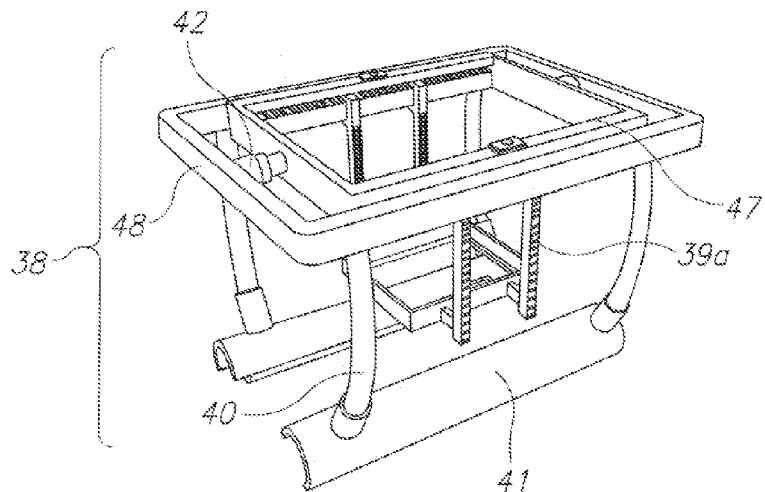
FIG. 7a is an angled top and front view of one possible embodiment of a free-standing precision surgical guide clamp 38 of the present invention.

FIG. 7*a* is an angled top and front view of one possible embodiment of a free-standing precision surgical guide clamp 38 of the present invention wherein are depicted precision attachment elements 39*a* designed to allow this embodiment's superstructure to remain above the level of the teeth so that the teeth adjacent to the implant site to do not interfere with the placement of the surgical templates in close proximity to the surface of the implant site. An inner frame 47 which swivels and twists on a swivel ball joint 42 is also depicted as well as one possible embodiment of clamping elements 41 to with flexible clamp arms 40 to secure the free-standing precision surgical guide clamp 38 to the vestibules of the jawbones within the mouth. An outer frame 48 is also depicted to which are attached the clamping elements 40, and 41 and the inner frame 47 of the free-standing precision surgical guide clamp 38.

Figure 7B:
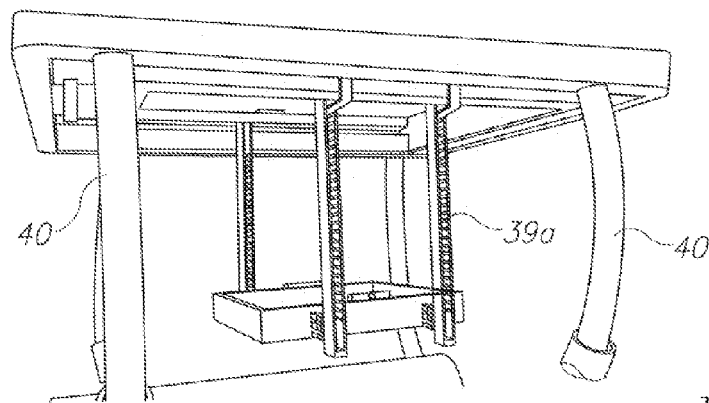

FIG. 7*b* is a close-up enlarged view of an embodiment of a segment of the free-standing precision surgical guide clamp 38 depicted in FIG. 7*a* wherein are depicted the precision attachment elements 39*a* and the flexible clamping arms 40.

Figure 7C:
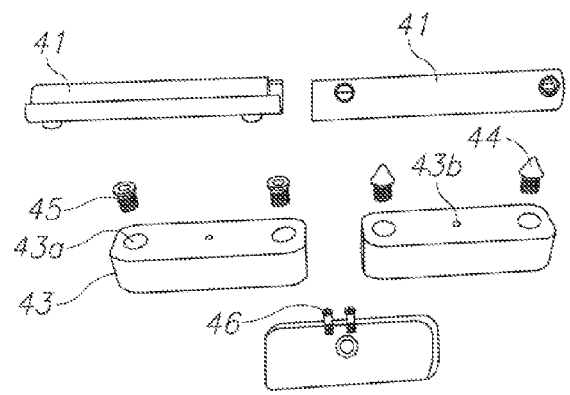
FIG. 7c is a top view of several possible embodiments of clamping attachments for the free-standing precision surgical guide clamp 38 depicted in FIGS. 7a and 7b.

FIG. 7*c* is a top view of several possible embodiments of clamping attachments for the free-standing precision surgical guide clamp 38 depicted in FIGS. 7*a* and 7*b* wherein are depicted other possible embodiments of clamping elements 43 with flat securing screws 45 or alternately securing screws with cleats 44 placed within the threaded shafts 43*a* and which along with the bone fixation screws 46 which are drilled through a self-limiting access hole 43*b* into the side alveolar ridges of the jawbone, allow for the optional more secure fixation of the free-standing precision surgical guide clamp 38 at the implant site.

Figure 8A:
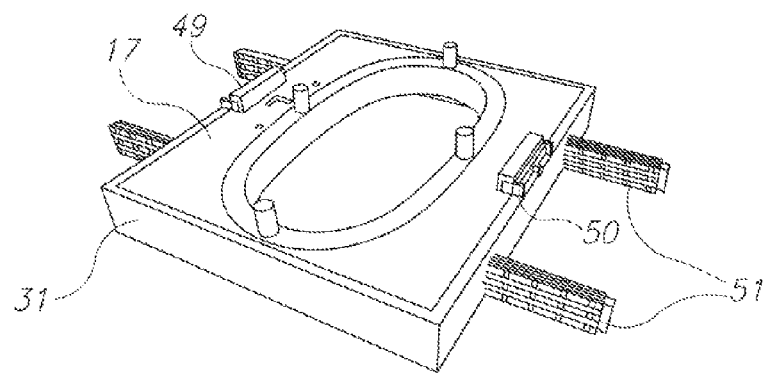
FIG. 8a is an angled top and side close-up view of one possible embodiment of the surgical template precision support insert 17 engaged within one possible embodiment of the surgical template precision support platform 31 of the present invention.

FIG. 8*a* is an angled top and side close-up view of one possible embodiment of the surgical template precision support insert 17 engaged within one possible embodiment of the surgical template precision support platform 31 of the present invention wherein are depicted possible embodiments of the platform precision adjustment element 51, as well as an embodiment of the securing sleeve 49 and sliding lock 50 to secure the surgical template precision support insert into the surgical template precision support platform.

Figure 8B:
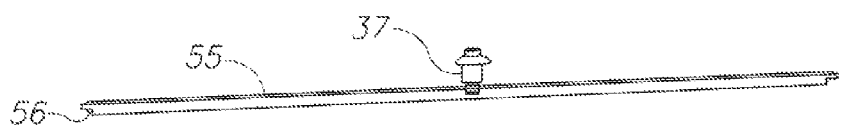
FIG. 8b is a front view of an embodiment of the securing bar 55 that can be dropped down to secure the precision attachment elements 39 and 39a of the precision surgical guide clamps 29 and 38.

FIG. 8*b* is a front view of one possible embodiment of the securing bar 55 that can be dropped down to secure the precision attachment elements 39 and 39*a* of the precision surgical guide clamps 29 and 38 at on specific location along their ratcheted internal rails 35 wherein are depicted as well the locking push button spring element 37 and counter springs 56 placed on the underside two ends of the securing bar 55.

Figures 8C, 8D:
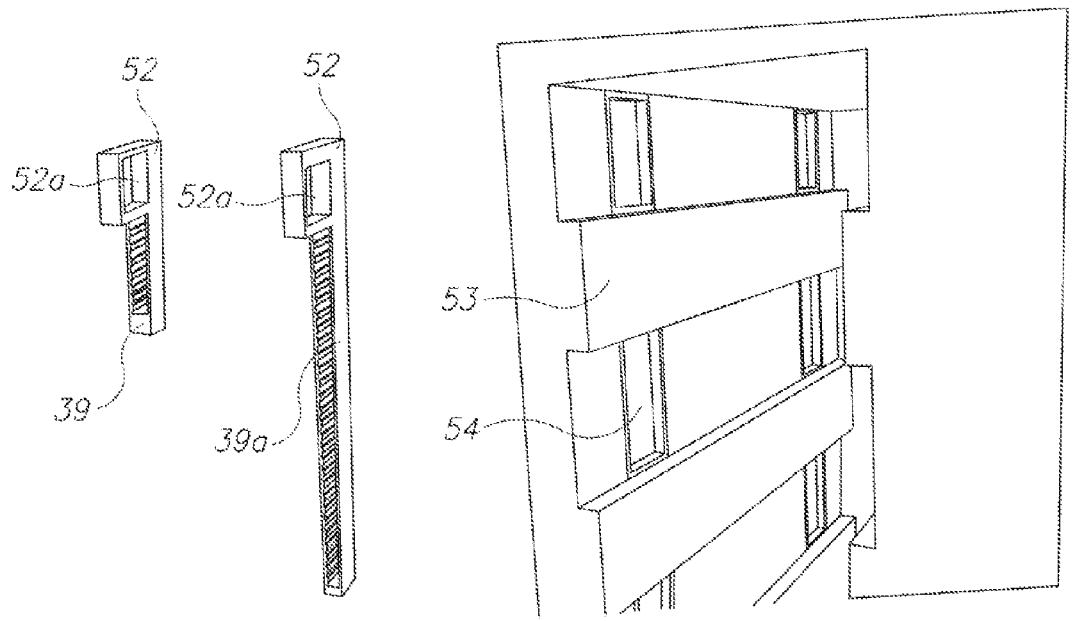
FIG. 8c is an angled front view of two possible embodiments of precision attachment elements 39 and 39a of the precision surgical guide clamps 29 and 38 of the present invention.
FIG. 8d is a close-up enlarged view from an angled front perspective of an embodiment of a segment of the precision attachment elements 39 and 39a depicted in FIG. 8c.

FIG. 8*c* is an angled front view of two possible embodiments of precision attachment elements 39 and 39*a* of the precision surgical guide clamps 29 and 38 of the present invention wherein are depicted possible embodiments of the center cut-out 52*a* of the head 52 of the precision attachment elements 39 and 39*a* which fit and slide through the ratcheted internal rails 35 of the respective precision surgical guide clamps 29 and 38.

FIG. 8*d* is a close-up enlarged view from an angled front perspective of a segment of the precision attachment elements 39 and 39*a* depicted in FIG. 8*c* wherein are depicted possible embodiments of the internal vertical height rails 53 as well as the lateral positioning notches 54 of the precision attachment elements 39 and 39*a*. These features allow for the accurate positioning and securing of the surgical templates 18 and 19 over the implant site.

Figure 9A:
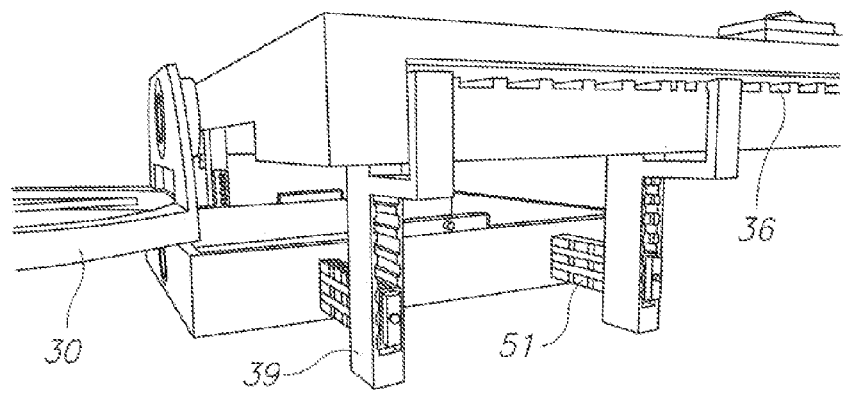
FIG. 9a is an angled close-up side view of an embodiment of a segment of the precision surgical guide clamp 28 depicted in FIG. 6a of the present invention.

FIG. 9*a* is an angled close-up side view of an embodiment of a segment of the precision surgical guide clamp 28 depicted in FIG. 6*a* of the present invention wherein are depicted the notched segments 36 of the ratcheted internal rails 35, the precision attachment elements 39, the clamp head 30 and the platform precision adjustment element.

Figure 9B:
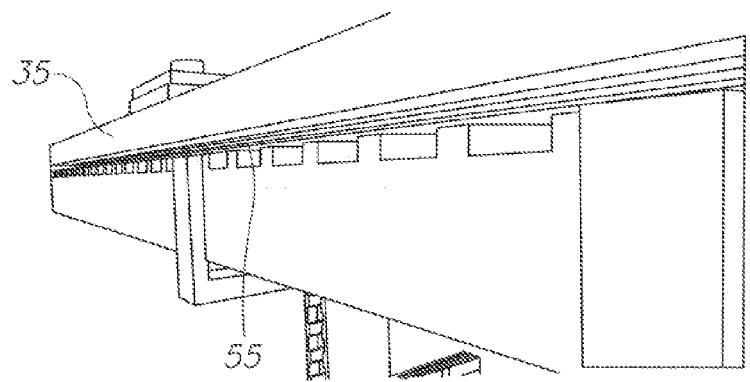

FIG. 9*b* is an even closer-up angled side view of an embodiment of a segment of the precision surgical guide clamp 29 depicted in FIG. 6*a* wherein are depicted the underside of the securing bar 55 as well as the ratcheted internal rail 35.

Figure 9C:
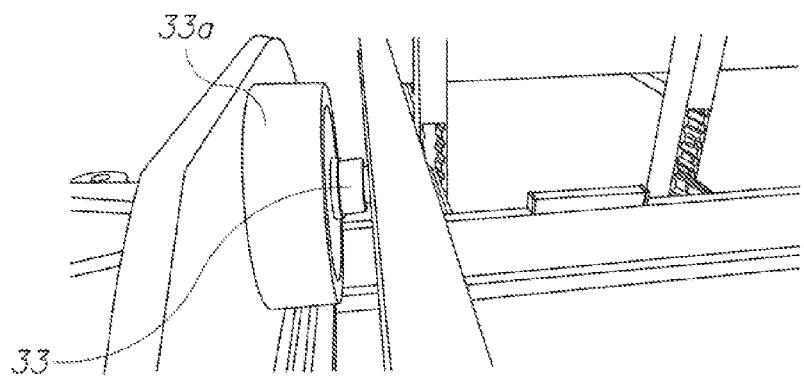

FIG. 9c is an angled close-up view from the top perspective of an embodiment of a different segment of the precision surgical guide clamp 29 depicted in FIG. 6a wherein is depicted one possible embodiment of the swivel ball joint 33 and the attachment element 33a.

Figure 10A:
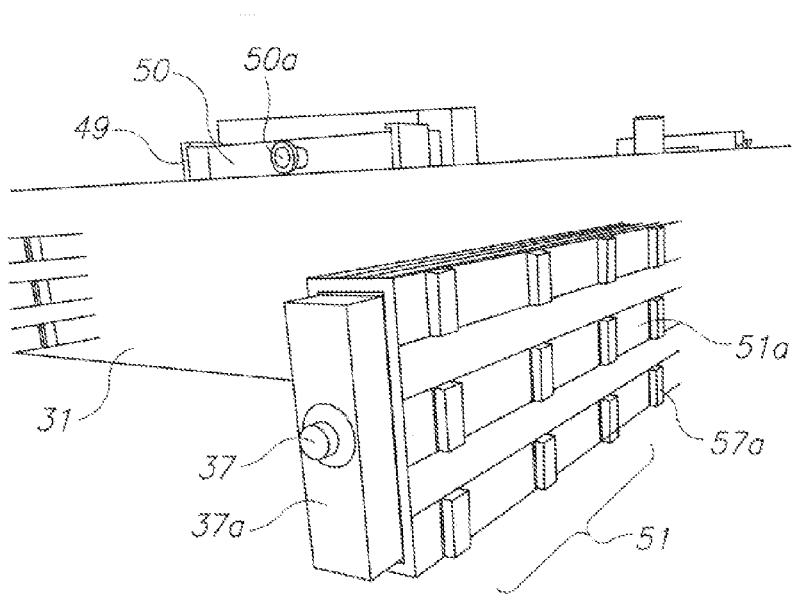

FIG. 10a is an angled close-up view from the side perspective of an embodiment of a segment of the surgical template precision support platform 31 and more specifically of the platform precision adjustment element 51 depicted in FIG. 8a wherein are depicted the locking element 37a of the locking push button spring loaded element 37 inserted within the external housing 51a of the platform precision adjustment element 51. Also depicted are possible embodiments of the securing sleeve 49, the sliding lock 50 and its handle 50a.

Figure 10B:
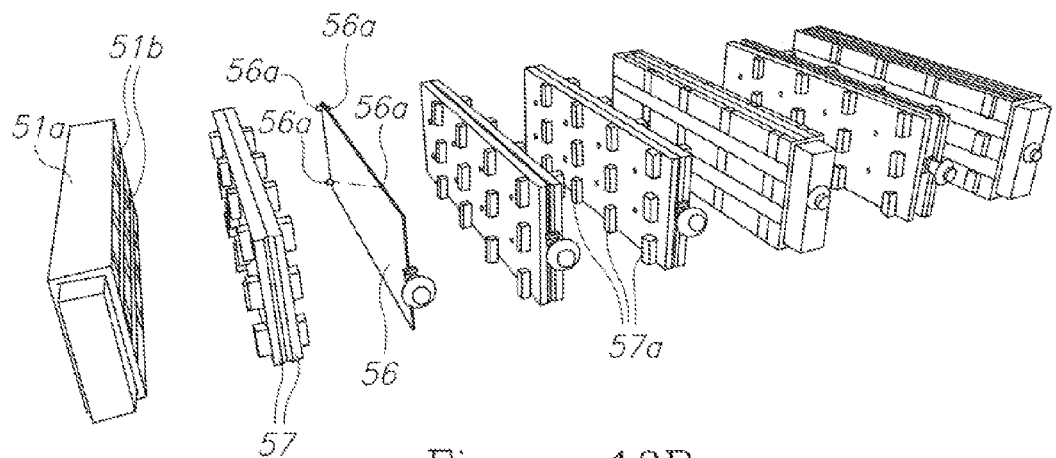

FIG. 10b illustrates an angled top view of the assembly (from left to right) of an embodiment of the parts needed to assemble the platform precision adjustment element 51 depicted in FIGS. 8a and 10a wherein are depicted the external housing 51a into which is inserted the following possible embodiments of the internal components: two expansion plates 57 with multiple projections on their outer surfaces 57a corresponding with the multiplicity of holes on either side of the outer walls of the external housing and meant to project through them to engage the lateral positioning notches 54 of the precision attachment elements 39 and 39a which are structural components of the precision surgical guide clamps 29 and 38, a center spreader plate 56 to which are attached four sets of spring-loaded spreader cylinders 56a that assist along with the locking push button spring loaded element 37 (when the push button mechanism is engaged) to evenly expand the two expansion plates 57 along their entire length within the external housing 51a and allow for the multiple projections 57a to "pop out".

Figure 10C:
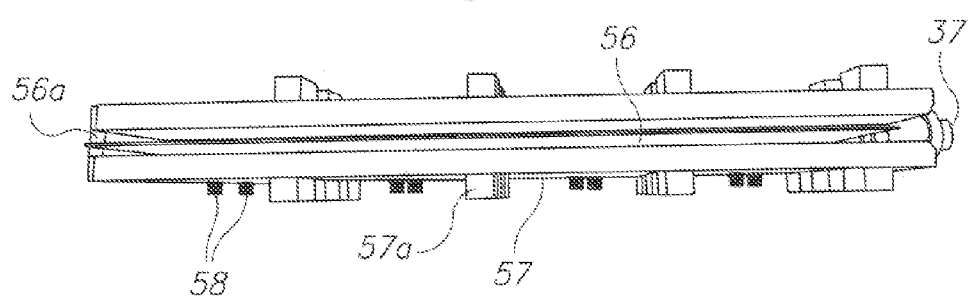
FIG. 10c is a close-up top view of an embodiment of the middle parts of the platform precision adjustment element 51 depicted in FIG. 10b.
Figure 11A:
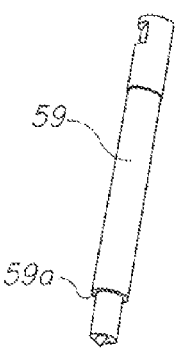
FIGS. 11a-11k are a series of top views of possible embodiments of the self-limiting bone drills 59, 61, 62, 63, 65, and 66; component drivers 60, 67, 68, 69 and surgical guide pin 64 of the present invention.
Figure 11B:
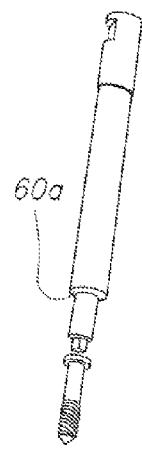
Figure 11C:
Figure 11D:
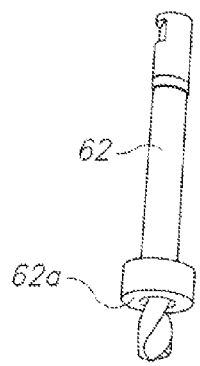
Figure 11E:
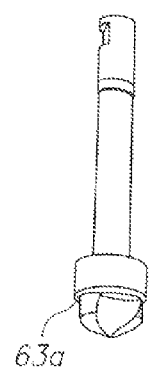
Figure 11F:
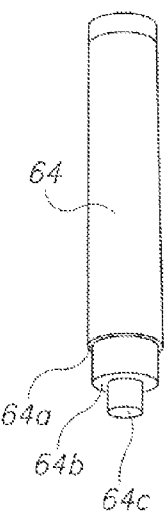
Figure 11G:
Figure 11H:
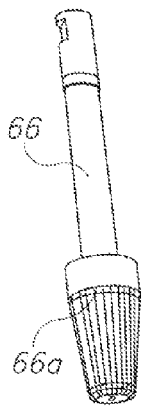
Figure 11I:
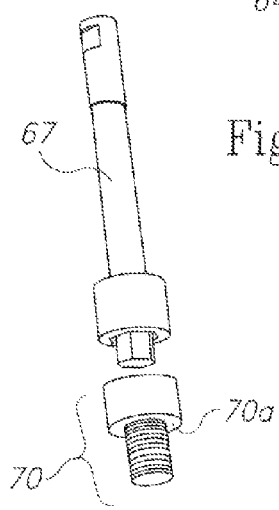
Figure 11J:
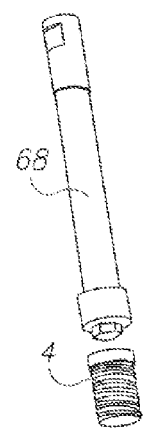
Figure 11K:
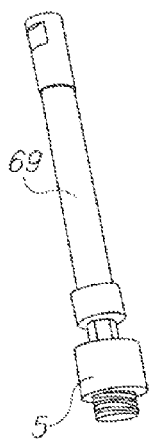

FIG. 10c is a close-up top view of an embodiment of the middle parts of the platform precision adjustment element 51 depicted in FIG. 10b wherein are depicted possible embodiments of a multiplicity of counter springs 58 located along the external surfaces of the expansion plates 57 which are located in positions within the external housing 51a to maintain the multiple projections 57a within the external housing as long as the locking push button spring loaded element 37 is not depressed inward (engaged).

FIGS. 11a-11k are a series of top views of possible embodiments of the self-limiting bone drills 59, 61, 62, 63, 65, and 66; component drivers 60, 67, 68, 69 and surgical guide pin 64 of the present invention wherein are depicted possible embodiments of the vertical depth self-limiting features 59a, 60a, 61a, 62a, 63a, 64a, 64b, 65a, 66a, and 70a. Also depicted are possible embodiments of the bone fixation screw 46, the root screw component carrier 70, a screw connector, and an abutment screw 5.

More specifically, a possible embodiment of the primary bone drill 61 with its unique self-limiting feature 61a which engages the circumferential template limiting flange of the primary surgical template 18 is depicted, as well as one possible embodiment of the self-limiting bore shaft finishing bone drill 66 for the final shaping of the bore shafts 74 of the final osteotomy 73.

Figure 12A:
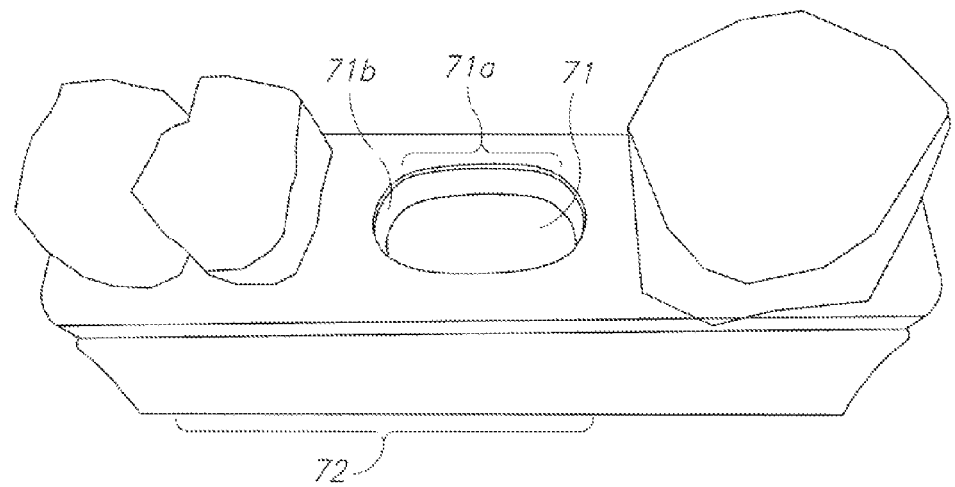
FIGS. 12a-12f depict a series of top views of the preparation of one possible embodiment of the osteotomy 73 and the insertion of one possible embodiment of components of the improved implant 77 of the present invention into the osteotomy 73.

FIG. 12a depicts a top view of the preparation of one possible shape of the osteotomy 73 wherein is depicted the head preparation 71, the level floor 71a of the head preparation 71 and the perpendicularly straight internal walls 71b of the head preparation 71 of the osteotomy.

Figure 12B:
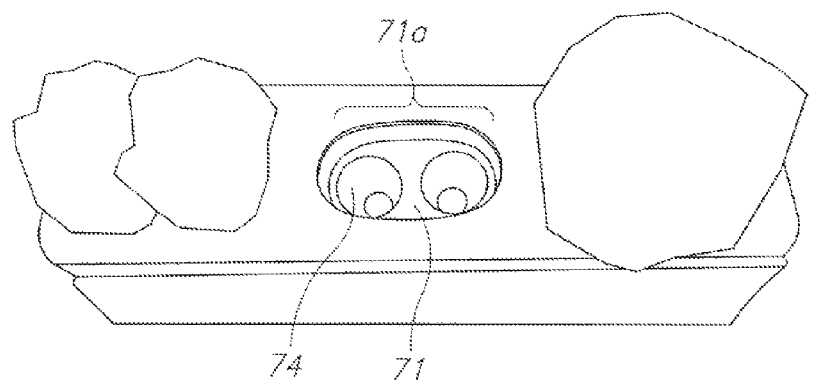

FIG. 12b depicts the finished osteotomy 73 at the implant site with one possible form of the head preparation 71 and bore shafts 74.

Figure 12C:
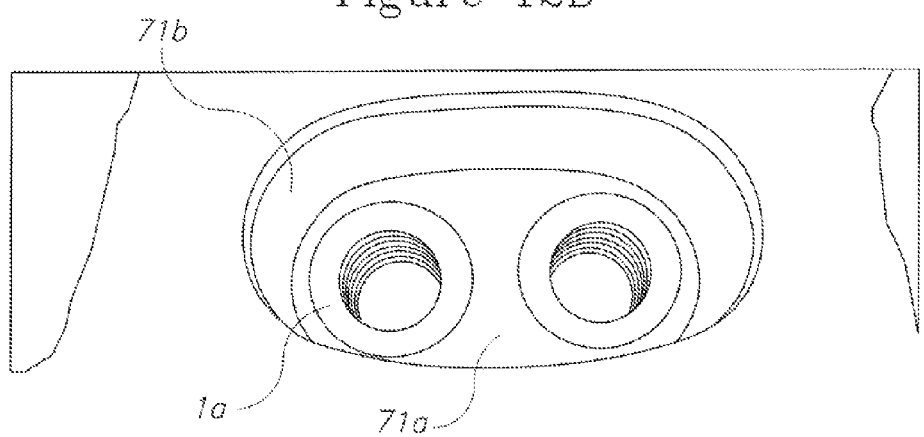

FIG. 12c depicts one possible embodiment of the non-threaded superior aspects 1a of two root screws 1 accurately inserted (in the completed bore shafts 74) in relation to the level floor 71a (exact depth) and internal side walls 71b of the head preparation so as to allow for the precise and intimate relation of the superior aspect 1a to the head component 2 or head/abutment component 6.

Figure 12D:
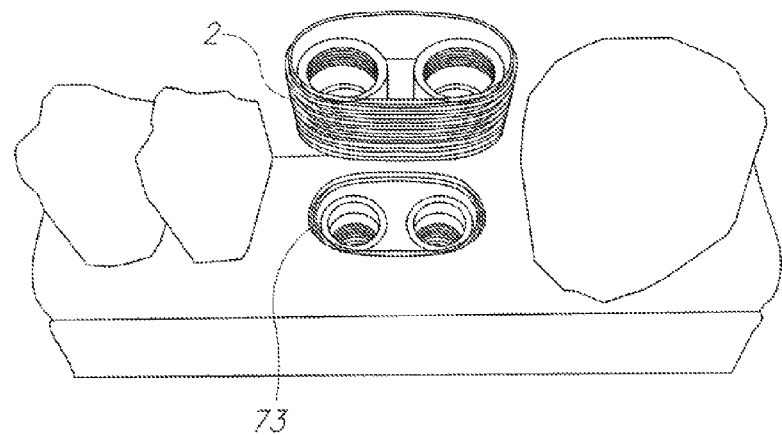

FIG. 12d depicts the insertion of one possible embodiment of the head component 2 of a three-stage implant of the present invention into the head preparation 71 of the osteotomy 73 and its intimate fit to the root screws 1 already inserted into the bore shafts 74 of the osteotomy 73.

Figure 12E:
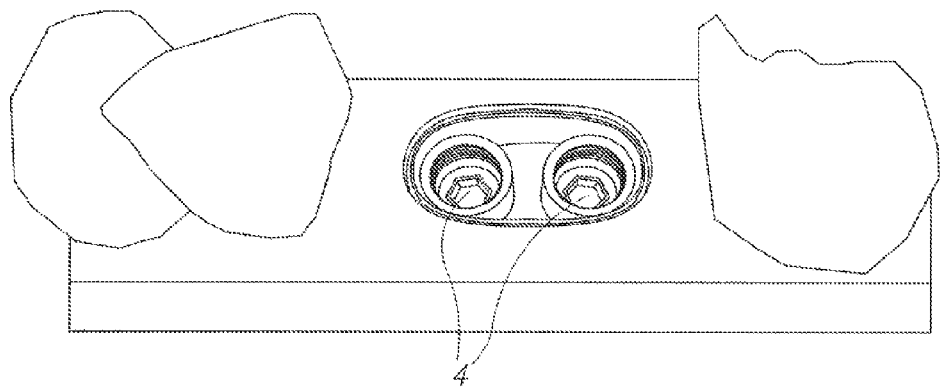

FIG. 12e depicts one possible embodiment of two screw connectors 4 secured within the internal connecting ring 7 of the head component 2 and securely connecting the head 2 to the root screws 1.

Figure 12F:
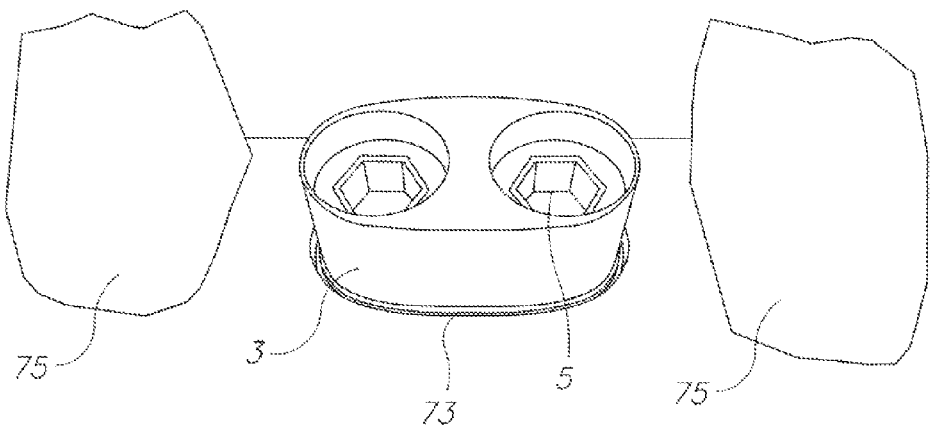

FIG. 12f depicts one possible embodiment of the abutment component 3 of the three-stage implant of the present invention secured into the internal hollowed form of the head component 2 via two abutment screws 5.

Figure 13A:
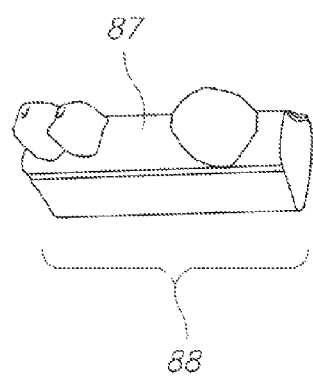
FIGS. 13a-13h depict a series of angled top views of one possible embodiment of the precision surgical guide clamp 29 clamped at one possible implant site which illustrate its use in preparing one possible embodiment of a multi-root osteotomy 73 for the insertion within it of one possible embodiment of the improved implant 77 of the present invention.

FIG. 13a depicts a segment of the upper jaw (maxilla) with a missing first molar tooth space 87.

Figure 13B:
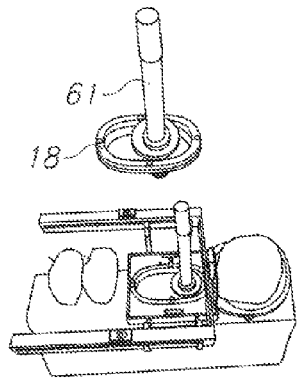

FIG. 13b depicts the primary bone drill 61 inserted into one possible embodiment of the primary surgical template 18 and engaged within the precision surgical guide clamp 29 at the implant site.

Figure 13C:
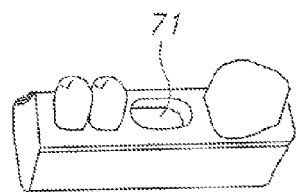

FIG. 13c depicts an embodiment of the completed head preparation 71 at the implant site prepared by utilizing the primary surgical template 18 of FIG. 13b.

Figure 13D:
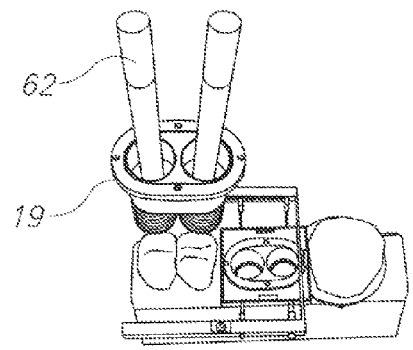

FIG. 13d depicts an embodiment of an initial pilot hole bone drill 62 inserted into one possible embodiment of the secondary surgical template 19 which is then placed down to the level of the floor 71a of the head preparation 71 while being engaged as well within the precision surgical guide clamp 29.

Figure 13E:
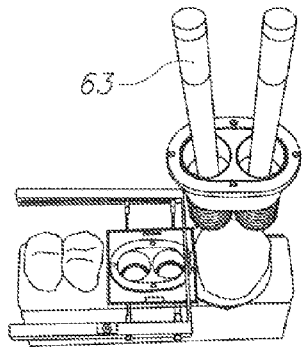

FIG. 13e depicts an embodiment of a secondary pilot hole bone drill 63 inserted (note that in the illustration there are two such drills for illustration purposes, though only one is needed and would actually be used sequentially in each of the access shafts 24 of the secondary surgical template 19) in the same secondary surgical template depicted.

Figure 13F:
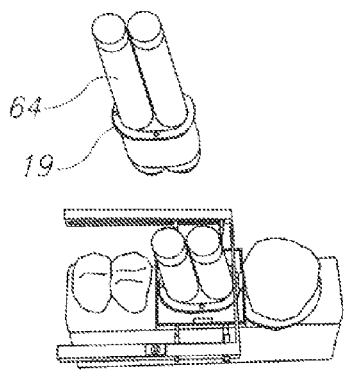

FIG. 13f depicts embodiments of two surgical guide pins which would both be placed into the secondary surgical template 19 to check the angulations and position of the pilot bore shafts in relation to the adjacent teeth.

Figure 13G:
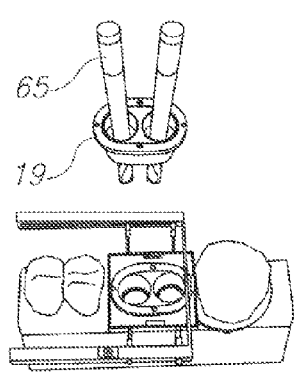

FIG. 13g depicts an embodiment of the final depth bore shaft bone drill 65 inserted into the secondary surgical template 19 (note that in the illustration there are two such drills for illustration purposes, though only one is needed and would actually be used sequentially in each of the access shafts 24 of the secondary surgical template 19).

Figure 13H:
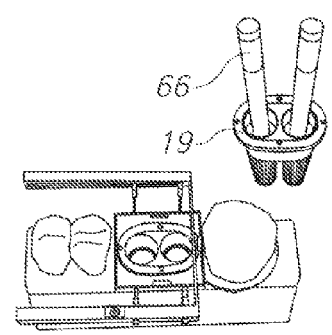

FIG. 13h depicts an embodiment of the bore shaft finishing bone drill 66 inserted into the secondary surgical template 19 (note that in the illustration there are two such drills for illustration purposes, though only one is needed and would actually be used sequentially in each of the access shafts 24 of the secondary surgical template 19) for completing the preparation of the bore shafts 74 of the osteotomy 73.

Figure 14:
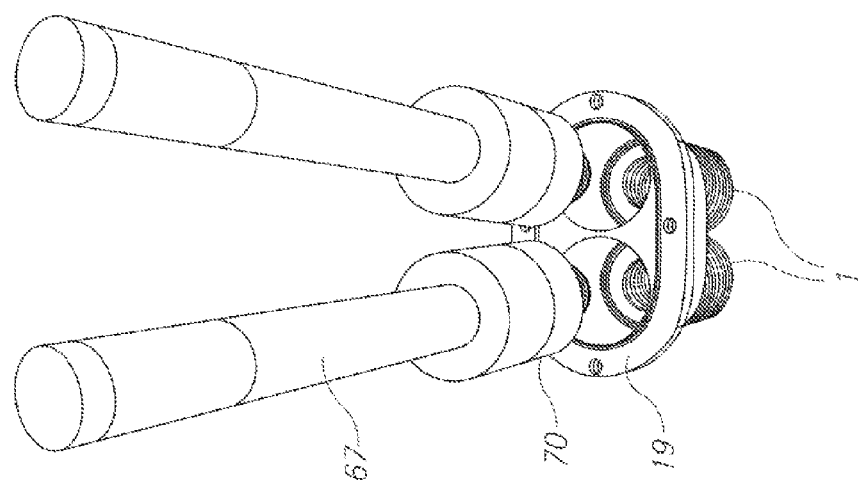
FIG. 14 is a close-up angled top view of one possible embodiment of a "root screw" component driver assembly composed of an implant carrier 70 and a slow speed driver 67, and one possible embodiment of the root screws 1 engaged within the self-limiting feature of one possible embodiment of the secondary surgical template 19.

FIG. 14 is a close-up angled top view of one possible embodiment of a "root screw" component driver assembly composed of an implant carrier 70 and a slow speed driver 67, and one possible embodiment of the root screws 1 engaged within the self-limiting feature of one possible embodiment of the secondary surgical template 19.

Figure 15:
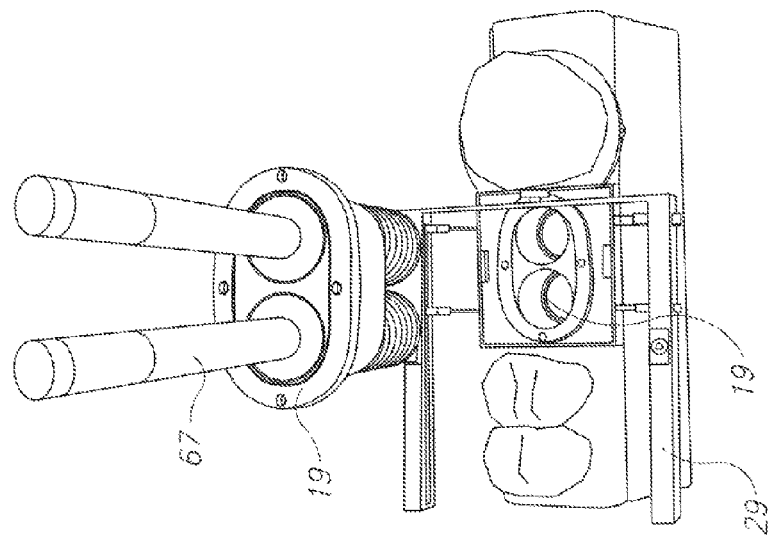

FIG. 15 depicts an angled top view of an embodiment of the driver assembly illustrated in FIG. 14 fully engaged within the secondary surgical template 19 of FIG. 14, and below that, the same surgical template 19 engaged within the precision guide clamp 29 depicted in FIG. 6a. The tools described above allow for the accurate insertion of the root screw components 1 in all three axes and the relation of these components to the head component 2 or head/abutment component 6 accurately in all three axes within the osteotomy 73 and in relation to the adjacent teeth.

Figure 16:
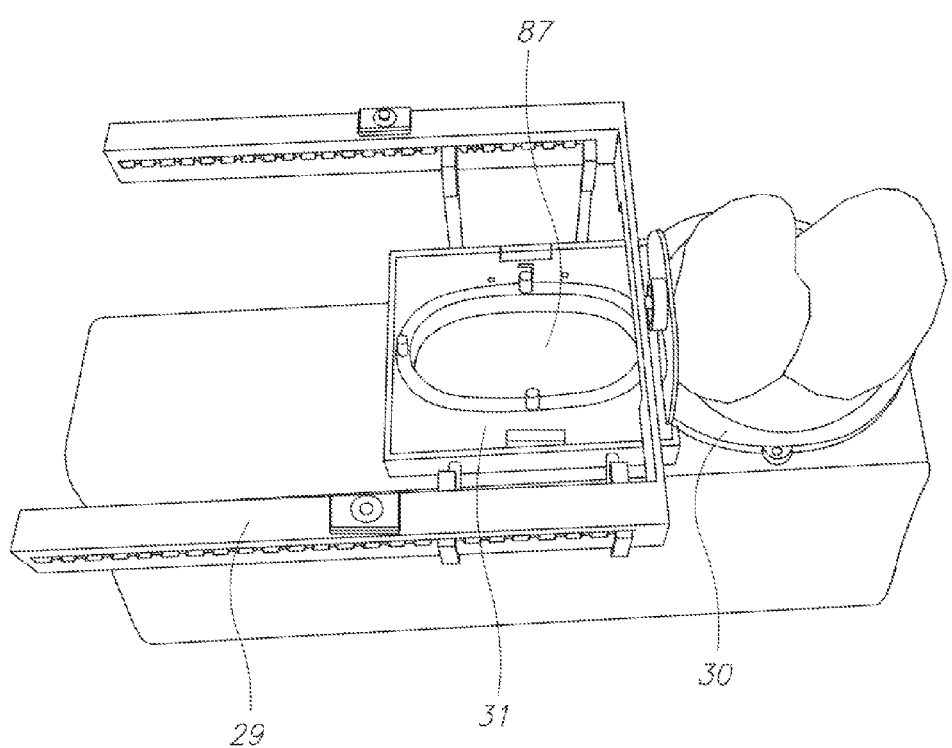
FIG. 16 is an angled top and side view of one possible embodiment of the precision surgical guide clamp 29 illustrating a free-end saddle situation for the implant site.

FIG. 16 is an angled top and side view of one possible embodiment of the precision surgical guide clamp 29 illustrating a free-end saddle situation for the implant site wherein are depicted the surgical template precision support platform 31 inserted into the precision surgical guide clamp 29 with one possible embodiment of a head clamp 30 clamped to two premolar teeth anterior to the first molar missing tooth implant site 87.

Figures 17A, 17B:
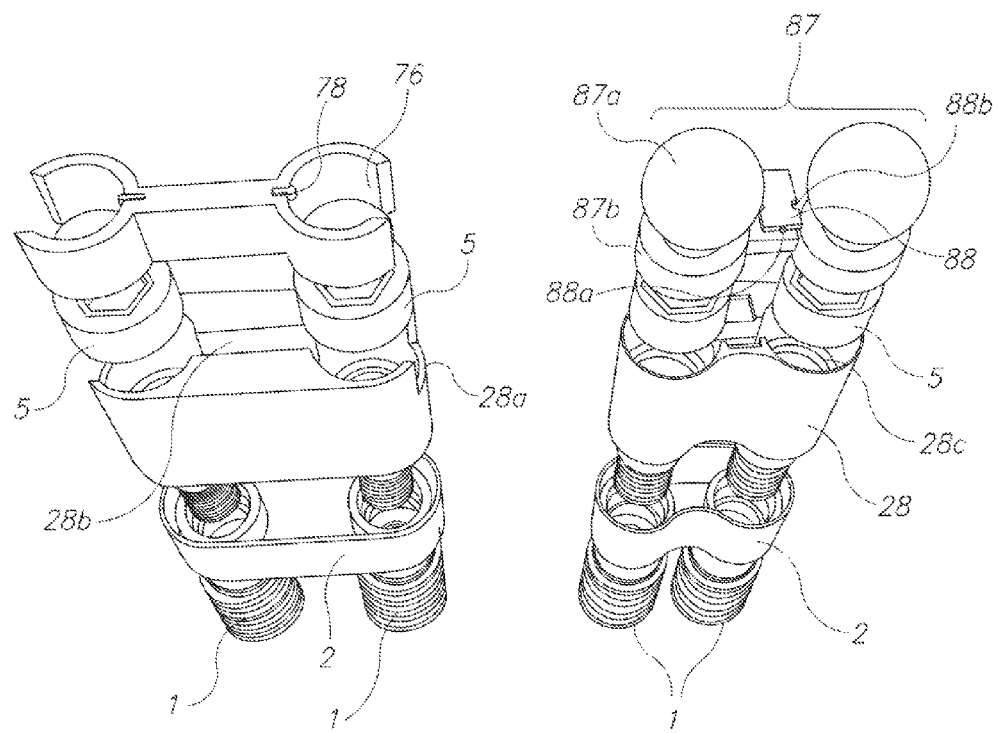
FIG. 17a is an angled top view of a vertical stacking of the components of one possible embodiment of the improved multi-root implant 77 specifically designed to support an over-denture and one possible embodiment of the over-denture connecting assembly locking element 76 of the present invention.
FIG. 17b is an angled top view of a vertical stacking of the components of one possible embodiment of the improved multi-root implant 77 specifically designed to accept the insertion of one possible embodiment of a double ball clip attachment design 87 for an overdenture (instead of an overdenture bar clip) to allow for the secure attachment of a full denture to the improved multi-root implant 77 of the present invention.

FIG. 17a is an angled top view of a vertical stacking of the components of one possible embodiment of a three-stage implant of the improved multi-root implant 77 specifically designed to support an over-denture and one possible embodiment of the over-denture connecting assembly component 76 of the present invention. Also depicted are possible embodiments of the over-denture abutment component 28 with cut-outs 28a on its mesial and distal aspects and a cut-out channel 28b running down its middle and oriented along the mesio-distal axis of the over-denture abutment 28. Further depicted is one possible embodiment of the head component 2, two root screw components 1, connector screws 4, abutment screws 5, and a locking feature 78 of the over-denture connecting assembly 76 which will be described in greater detail below.

FIG. 17b is an angled top view of a vertical stacking of the components of one possible embodiment of the improved multi-root implant 77 specifically designed to accept the insertion of one possible embodiment of a double ball clip attachment design 87 for an overdenture (instead of an over-denture bar clip) to allow for the secure attachment of a full denture to the improved multi-root implant 77 of the present invention. Also depicted is a locking element 88 with two spring loaded buttons on two of its side aspects in order to engage the cut-out surface 28c of the over-denture abutment 28 and engage as well corresponding concave shafts in said cut-out 28c in order to securely lock the double ball clip 87 into the over-denture abutment 28.

Figure 18:
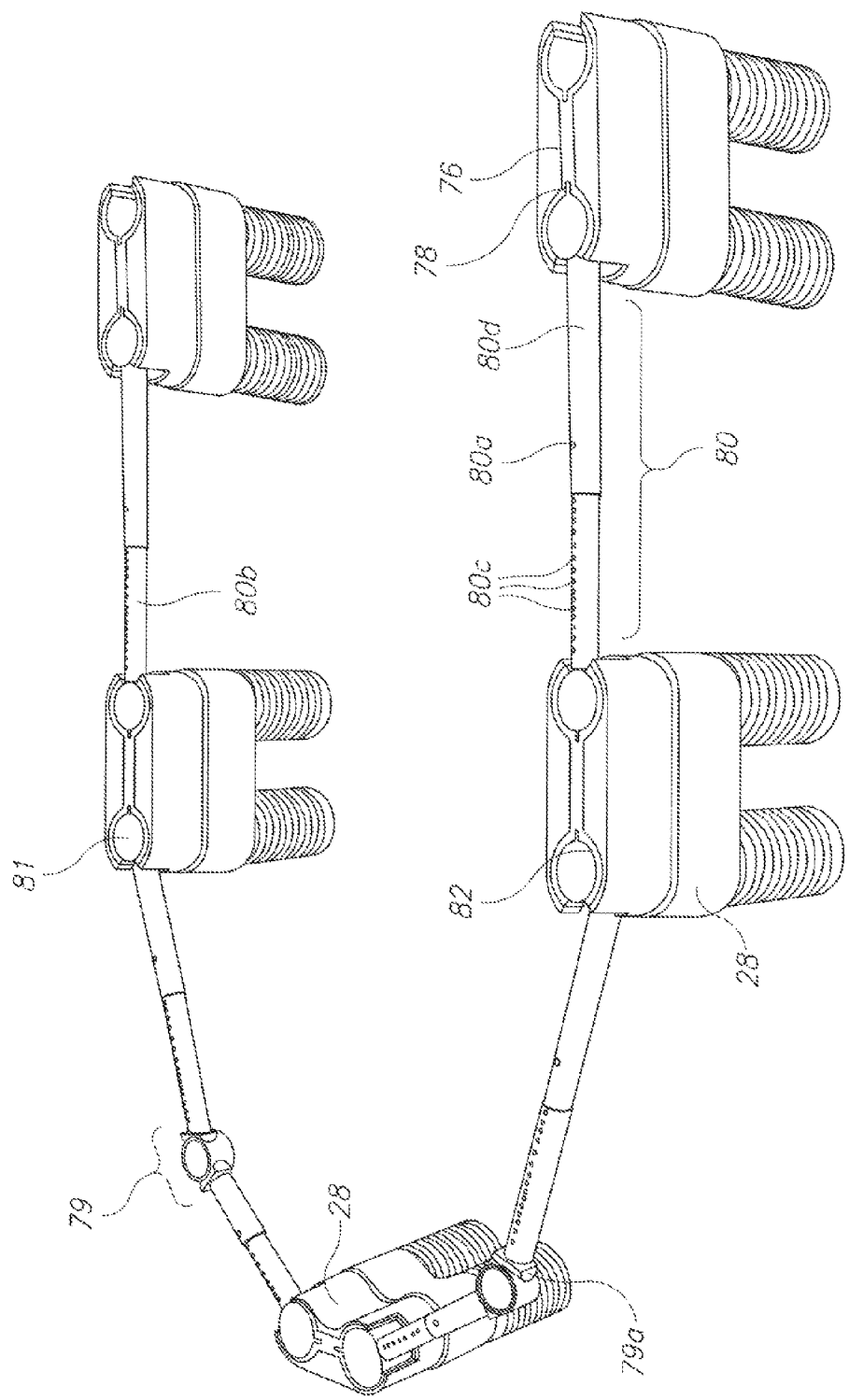
FIG. 18 is an angled top view of one possible assembly embodiment of several possible embodiment of the multi-root improved implant 77 of the present invention wherein is depicted overdenture connecting assembly components, 76, 79, 80 and 81 engaged within these implant in order to allow for a fixed full arch support for a removable full denture in an edentulous patient.

FIG. 18 is an angled top view of one possible overdenture connecting assembly embodiment for connecting multiple assembly components, using the multi-root improved implant 77 of an embodiment of the present invention as the anchors for the overdenture assembly. As can be seen in the figure, overdenture connecting assembly components, 76, 79, 80 and 81 may engage within the over-denture abutments 28 of the improved implants 77 of the present invention in order to allow for a fixed full arch support for a removable full denture in an edentulous patient. Also depicted is the rotating head 81 which allows for the connection of multiple implants that are not non-parallel along their rotational axes. Depicted as well is an embodiment of length adjustment features 80a (a locking screw) and multiple shafts 80c (for the set screw 80a to engage) along the top surface of the smaller diameter sliding cross-member 80b which intimately slides into the internal shaft of the larger diameter cross-member 80d. Also illustrated is one possible embodiment of the hinge element 79 is which connects two cross-members 80 and allows for the adjusting their angle to each other. The hinge element assembly 79 with its center rotating hinge 79a also contains two swiveling features 79b on either side of the hinge element 79 which allow for the adjustment of the angled vertical axis of the cross-members 80, useful in relating implants that sit at different heights in the jawbone.

Figure 19A:
FIGS. 19a-19e are a series of close-up top view of possible embodiments of the connecting assembly components 76, 79, 80 and 81 depicted in FIG. 18.
Figure 19B:
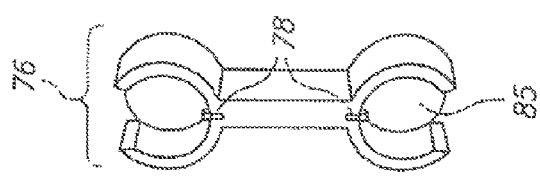

FIGS. 19a and 19b are a close-up top view of two possible embodiments of the connecting assembly components 76, 79, and 80 depicted in FIG. 18 wherein are depicted a hinge element assembly 79 whose center rotating hinge 79a allows for a change in the angular relation of the two adjustable length cross-members 80 attached to it. The cross-members 80 have attached to them rotating heads 81 with notched concavities on their top surfaces 82 for the engagement of the locking features 78 of the over-denture connecting assembly component 76 into these notches to lock it in place.

Figure 19C:
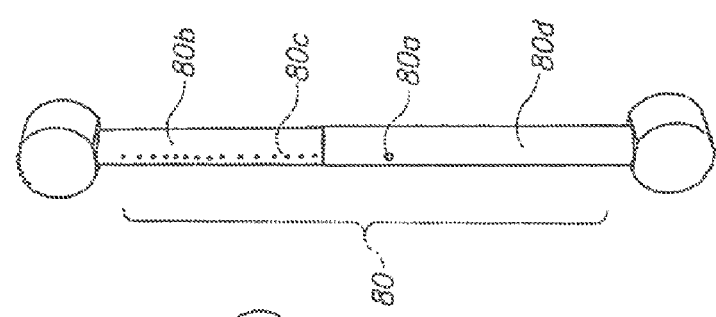

FIG. 19c is a close-up top view of one possible embodiment of a single cross-member with two rotating heads 81 attached to it and which also depicts the smaller diameter cross-member section 81b which slides into the hollowed center shaft of the larger diameter cross-member 80d which allows for adjusting the over-all length of the cross-member 80. Additionally, depicted are possible embodiments of the locking features 80a (set screw) and notched shafts 80c for the engagement of the set screw 80a within them.

Figure 19D:
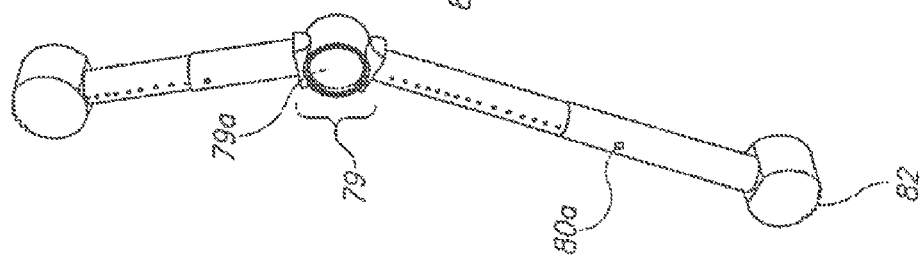

FIG. 19d is a close-up top view of possible embodiments of cut-outs 84 of one possible embodiment of the over-denture connecting assembly component 76 that allow for the insertion of the terminal rotating heads 81 of the connector bars 80, a limiting floor 85 of the connecting assembly component 76, limiting curved elements 83 of the connector assembly component 76, a short connecting bar 86 (which is an integral part of the connecting assembly component 76) and which intimately fits into the cut-out 28a of the over-denture abutment component 28 of the present invention.

Figure 19E:
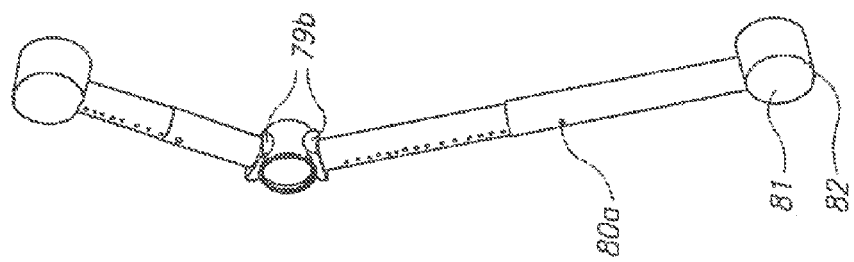

FIG. 19e is a close-up top view of another possible embodiment of the connecting assembly component 76 illustrating a shorter length integral connecting bar 86 to fit a shorter mesio-distal length multi-root implant overdenture abutment component 28.

Figure 20C:
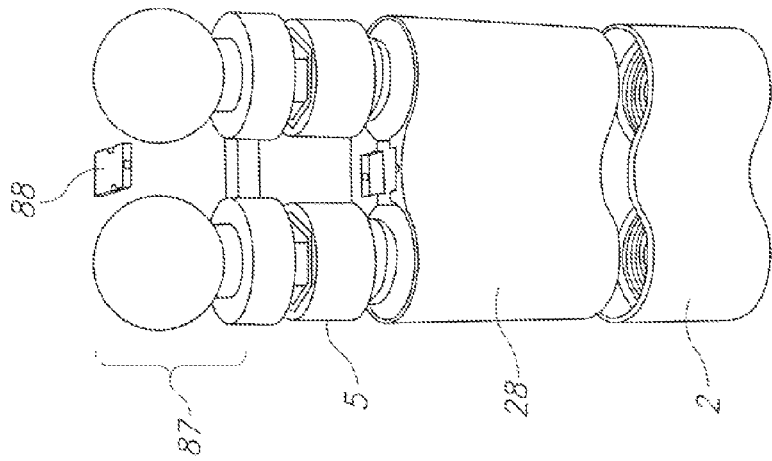
FIGS. 20a-20c are a series of front views of one possible embodiment of a two stage overdenture head/abutment component 6a and two possible embodiments of three stage overdenture abutments made of components 3 coupled with 89 and 28 coupled with 87.
Figure 20B:
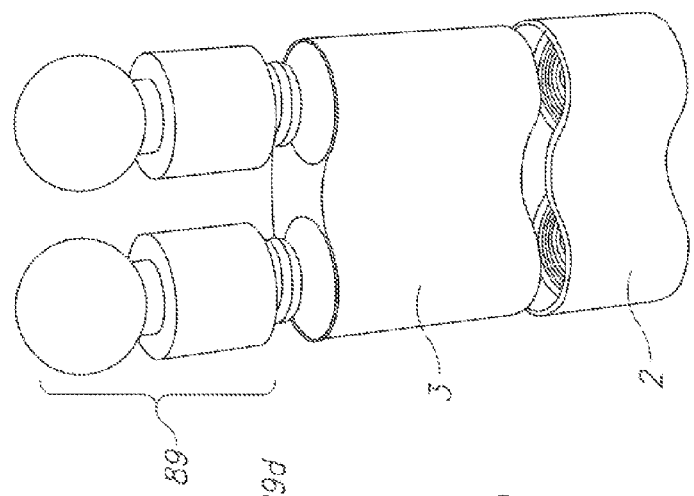
Figure 20A:
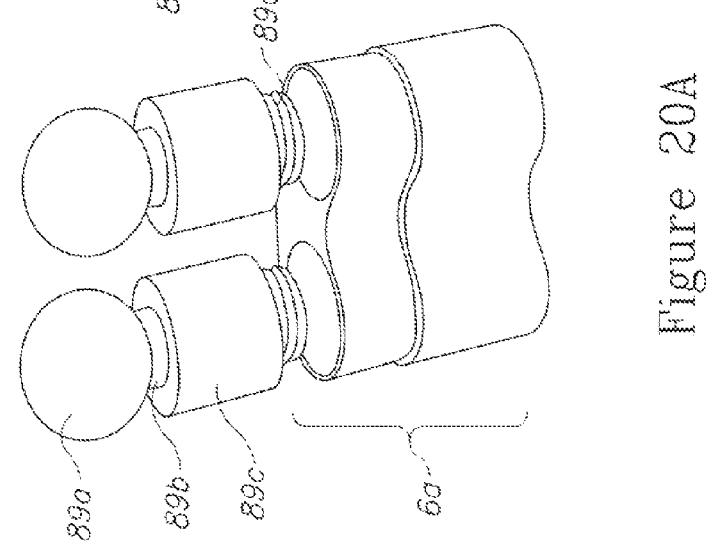

FIG. 20a is a front view of one possible embodiment of a vertical stacking of a two stage over-denture head/abutment 6a into which is inserted two separate over-denture ball clips. Also depicted are the ball segment 89a, the neck segment 89b the screw shank 89c and the threaded screw segment 89d of the over-denture ball clip 89.

FIG. 20b is a front view of one possible embodiment of a vertical stacking of a three stage configuration wherein are depicted possible embodiments of a separate head component 2, an abutment component 3 and two separate overdenture ball clips 89.

FIG. 20c is a front view of another possible embodiment of a vertical stacking of a three stage configuration wherein are depicted possible embodiments of a separate head component 2, an over-denture abutment 28, two abutment screws 5, and a one piece over-denture double ball clip 87 and locking element 88.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A dental bone implant comprising:
   i. a single bone attachment component for securing the implant into a bone, wherein the bone attachment component includes an internally threaded bore, a distal end and a proximal end, the entire length of the bone attachment component being adapted for implantation into a jawbone, wherein the distal end of the bone attachment component has a distal surface;

ii. a single head component independent of and separable from the attachment component, wherein the head component has a length, a bore going through the head component and extending the length of the head component from a proximal end to a distal end, the bore having from proximal end to distal end: a set ring, a flange opening, an unthreaded section, and a threaded section, the bore of the head component comprising an internal limiting flange between the set ring and the threaded section, wherein the entire length of the head component is adapted for implantation into the bone and is further adapted to be secured to the bone attachment component utilizing the internal limiting flange at the time of initial implantation of both the bone attachment component and the head component into the bone and is further adapted to be secured to an additional component using the threaded section of the bore, and the head component has a cross-section outer wall shape perpendicular to the length of the head component, wherein the cross-section outer wall shape is generally uniform along the length of the head component and the cross-section outer wall shape is non-circular; and iii. an abutment adapted to be secured independently to the head component in an overlying relation to the head component, for receiving a prosthesis, and being spaced apart from the bone attachment component by the head component, wherein the abutment is adapted for extending above the crestal height of the bone;

wherein the abutment includes a bare hole including an internal limiting flange, wherein the bore hole of the abutment and the bore of the head component is a set of corresponding bores that are axially aligned.

2. The implant of claim 1, wherein the implant includes a head connector component that secures the head component to the bone attachment component utilizing the internal limiting flange of the head component at the time of initial implantation of the head component and the bone attachment component into the bone so that a proximal surface of the head component rests on the distal end of the bone attachment component; wherein the head connector component secures only the head component to the bone attachment component; and the set ring of the head component is a concave set ring that allows for an intimate seating of the distal end of the bone attachment component into an under surface of the head component.

3. The implant of claim 2, wherein the head connector component is a head connector screw having a threaded shaft and a distal screw head, the internal limiting flange of the bore of the head component separates the distal head of the head connector screw from the bone attachment component, and the threaded shaft of the head connector screw engages the internally threaded bore of the bone attachment component.

4. The implant of claim 2, wherein the head connector component connects the head component directly to the bone attachment components.

5. The implant of claim 1, wherein the implant further includes a connector, wherein the connector engages a distal end of the bore of the head component secures the abutment to the head component.

6. The implant of claim 1, wherein the cross-section outer wall shape of the head component approximates the natural cross sectional form of a root of a tooth, wherein the cross-section outer wall shape is an oval, a rhomboid, or a kidney-shape, and the abutment is shaped to provide a substantially rotation-free fit relative to the head component.

7. The implant of claim 1, wherein the bore of the head component has a first diameter that extends from opposing ends of the head component for receiving a head connector component; the bone attachment component is a headless screw having i) a generally cylindrical threaded outer surface profile for engaging a bone; and ii) a distal shaft section having an outer diameter that is larger than the first diameter of bore of the head component.

8. The implant of claim 1, wherein the abutment includes an element for anchoring a denture directly to the abutment.

9. The implant of claim 1, wherein the head component is a single monolithic element.

10. The dental bone implant of claim 1 wherein, the bone attachment component is a root screw having a generally cylindrical shape;

the corresponding bores overlies the internally threaded bore of the root screw;

the cross-section outer wall shape of the head component is an oval, a rhomboid, or a kidney-shape;

wherein the bore hole of the abutment is capable of receiving a screw head of an abutment connector screw and the limiting flange of the abutment is capable of maintaining the screw head of the abutment connector screw in the bore hole of the abutment with a shaft of the abutment connector screw extending into the bore hole of the head component; and the number of abutments is one and the number of head components is one.

11. The dental implant of claim 10 wherein the implant includes a head connector screw for directly securing the head component to the root screw.

12. The dental implant of claim 10 wherein the only components of the bone implant for contacting the bone are the bone attachment component and the head component.

13. A dental bone implant comprising:

i. a head component having a length, a proximal end and a distal end, and containing two or more bores including a first bore and a second bore, wherein the first and second bores of the head component each extend the length of the head component from the proximal end to the distal end, the first and second bore each having from proximal end to distal end: a set ring, a flange opening, and a threaded section, the first and second bore each having an internal limiting flange between the set ring and the threaded section, such that the head component comprises two or more internal limiting flanges, the head component having a generally constant oval outer cross-section along the length and is entirely adapted for implantation into a jaw bone;

ii. a plurality of headless root screws independent of and separable from the head component having a length including a first root screw and a second root screw, wherein the entire length of each of the first and second root screws is adapted for implantation into a jaw bone, wherein the first and second root screws each: includes an externally threaded shaft, has a distal end, and has an internal threaded bore on the distal end;

iii. a multiple of head connector screws including a first head connector screw and a second head connector screw, wherein each of the first and second head connector screw has a screw head and an externally threaded shaft, wherein the first head connector screw is for attaching the head component directly to the first root screw by inserting the externally threaded shaft through the distal end of the first bore of the head component, and screwing the externally threaded shaft into the internally threaded bore of the first root screw, utilizing the internal limiting flange of the first bore of the head component to receive fastening pressure from the first head connector screw and to separate the screw head from the root screw, and the second head connector screw is for attaching the head component directly to the second root screw utilizing the internal limiting flange of the second bore of the head component, so that the head component rests distally on the first and second root screws;

iv. an abutment component attachable to the head component in overlying relation to the head component for receiving a dental prosthesis and being spaced apart from the plurality of root screws by at least the head component, wherein the abutment includes a first abutment bore hole axially aligned with the first bore of the head component and having an internal limiting flange, and a second abutment bore hole axially aligned with the second bore of the head component and having an internal limiting flange; and v. a first abutment screw and a second abutment screw each including a screw head and an externally threaded shaft, wherein the abutment screws secure the abutment component to the head component; wherein the screw head of the first head connector screw has a length that is sufficiently short so that the internally threaded portion of the first bore of the head component is available for receiving the threaded shaft of the first abutment screw for securing the abutment directly to the head component;

the and second bores of the head component each extend from opposing ends of the head component;

the screw head of the first head connector screw is positioned in the first bore of the head component so that a distal surface of the screw head is recessed between the ends of the head component by the internal limiting flange of the first bore, and the screw head of the second head connector screw is positioned in the second bore of the head component so that a distal surface of the screw head is recessed between the ends of the head component by the internal limiting flange of the second bore;

the first head connector screw connects the head component, the first root screw, and the first head connector screw by threaded engagement of the threaded shaft of the first head connector screw with the internally threaded bore of the first root screw, and the second head connector screw connects the head component, the second root screw, and the second head connector screw by threaded engagement of the threaded shaft of the second head connector screw with the internally threaded bore of the second root screw;

the threaded external shafts of each of the first and second root screws has an outer diameter that is larger than the diameter of the bore of the head component to which it is attached; and the implant is configured so that it can be implanted into an oval bony recess, which is defined by a floor surface and an oval peripheral side wall formed in a jaw bone, so that each of the first and second root screws threadably engages the jaw bone in holes that extend into the jaw bone from the floor surface of the bony recess, the head component overlies the plurality of root screws and also engages the floor, each of the multiple of connector screws connects the head component with one of the first and second root screws, and the abutment component overlies the head component and is connected to it with the first and second abutment screws.

14. The dental bone implant of claim 13, wherein the first and second root screws each have generally cylindrical shape;

the first abutment bore hole axially aligned with the first bore of the head component are a first set of corresponding bores, wherein the first set of corresponding bores overlies the internally threaded bore of the first root screw;

wherein the first bore hole of the abutment is capable of receiving a screw head of the first abutment screw; wherein the first abutment screw has a shaft, and the limiting flange of the first bore hole of the abutment is capable of maintaining the screw head of the first abutment screw in the bore hole of the abutment with the shaft of the first abutment screw extending into the bore hole of the head component; and the number of abutments is one and the number of head components is one.

15. The dental implant of claim 14 wherein the only components of the bone implant for contacting the bone are the root screws and the head component.

16. The dental implant of claim 13 wherein the first and second bore of the head component each having from the proximal end to the distal end: the set ring, the flange opening, an unthreaded section, and the threaded section, the first and second bore each having the internal limiting flange partly separating the set ring from the unthreaded section.

* * * * *

UNITED STATES PATENT AND TRADEMARK OFFICE
CERTIFICATE OF CORRECTION

| | | |
|---|---|---|
| PATENT NO. | : 8,827,704 B2 | Page 1 of 1 |
| APPLICATION NO. | : 13/146038 | |
| DATED | : September 9, 2014 | |
| INVENTOR(S) | : Daniel Sanders | |

It is certified that error appears in the above-identified patent and that said Letters Patent is hereby corrected as shown below:

In the Claims,
Column 37, Claim 1, Line 34, "bare" should be "bore"
Column 39, Claim 13, Line 37, insert --first-- before "and"

Signed and Sealed this
Ninth Day of December, 2014

Michelle K. Lee
*Deputy Director of the United States Patent and Trademark Office*